(12) United States Patent
Putnam et al.

(10) Patent No.: US 9,715,573 B2
(45) Date of Patent: Jul. 25, 2017

(54) NUCLEIC ACID SEQUENCE ASSEMBLY

(71) Applicant: Dovetail Genomics, LLC, Santa Cruz, CA (US)

(72) Inventors: Nicholas H. Putnam, Santa Cruz, CA (US); Jonathan C. Stites, Santa Cruz, CA (US); Brandon J. Rice, Santa Cruz, CA (US)

(73) Assignee: DOVETAIL GENOMICS, LLC, Bethesda, MD (US)

( * ) Notice: Subject to any disclaimer, the term of this patent is extended or adjusted under 35 U.S.C. 154(b) by 0 days.

(21) Appl. No.: 15/045,818

(22) Filed: Feb. 17, 2016

(65) Prior Publication Data

US 2016/0246922 A1    Aug. 25, 2016

Related U.S. Application Data

(60) Provisional application No. 62/117,256, filed on Feb. 17, 2015, provisional application No. 62/294,208, filed on Feb. 11, 2016.

(51) Int. Cl.
*G06F 19/22* (2011.01)
*C12Q 1/68* (2006.01)

(52) U.S. Cl.
CPC .......... *G06F 19/22* (2013.01); *C12Q 1/6874* (2013.01)

(58) Field of Classification Search
None
See application file for complete search history.

(56) References Cited

U.S. PATENT DOCUMENTS

| | | | |
|---|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,988,617 A | 1/1991 | Landegren et al. |
| 5,143,854 A | 9/1992 | Pirrung et al. |
| 5,234,809 A | 8/1993 | Boom et al. |
| 5,242,794 A | 9/1993 | Whiteley et al. |
| 5,348,853 A | 9/1994 | Wang et al. |
| 5,476,930 A | 12/1995 | Letsinger et al. |
| 5,494,810 A | 2/1996 | Barany et al. |
| 5,567,583 A | 10/1996 | Wang et al. |
| 5,571,639 A | 11/1996 | Hubbell et al. |
| 5,593,839 A | 1/1997 | Hubbell et al. |
| 5,705,628 A | 1/1998 | Hawkins |
| 5,780,613 A | 7/1998 | Letsinger et al. |
| 5,786,146 A | 7/1998 | Herman et al. |
| 5,837,832 A | 11/1998 | Chee et al. |
| 5,989,823 A | 11/1999 | Jayasena et al. |
| 5,994,056 A | 11/1999 | Higuchi |
| 6,033,854 A | 3/2000 | Kurnit et al. |
| 6,110,709 A | 8/2000 | Ausubel et al. |
| 6,117,635 A | 9/2000 | Nazarenko et al. |
| 6,171,785 B1 | 1/2001 | Higuchi |
| 6,174,670 B1 | 1/2001 | Wittwer et al. |
| 6,225,109 B1 | 5/2001 | Juncosa et al. |
| 6,287,766 B1 | 9/2001 | Nolan et al. |
| 6,326,145 B1 | 12/2001 | Whitcombe et al. |
| 6,416,950 B1 | 7/2002 | Lohse et al. |
| 6,449,562 B1 | 9/2002 | Chandler et al. |
| 6,582,938 B1 | 6/2003 | Su et al. |
| 6,787,308 B2 | 9/2004 | Balasubramanian et al. |
| 6,833,246 B2 | 12/2004 | Balasubramanian |
| 6,897,023 B2 | 5/2005 | Fu et al. |
| 6,969,488 B2 | 11/2005 | Bridgham et al. |
| 7,001,724 B1 | 2/2006 | Greenfield |
| 7,361,468 B2 | 4/2008 | Liu et al. |
| 7,414,117 B2 | 8/2008 | Saito et al. |
| 7,425,415 B2 | 9/2008 | Pfeifer et al. |
| 7,709,179 B2 | 5/2010 | Iwashita |
| 7,709,197 B2 | 5/2010 | Drmanac |
| 7,901,891 B2 | 3/2011 | Drmanac |
| 7,985,546 B2 | 7/2011 | Church et al. |
| 8,058,004 B2 | 11/2011 | Oleinikov |
| 8,071,296 B2 | 12/2011 | Ruan et al. |
| 8,076,070 B2 | 12/2011 | Chen et al. |
| 8,153,373 B2 | 4/2012 | De Laat et al. |
| 8,278,112 B2 | 10/2012 | Shokat et al. |
| 8,367,322 B2 | 2/2013 | Barany et al. |

(Continued)

FOREIGN PATENT DOCUMENTS

| EP | 0476014 A1 | 3/1992 |
| EP | 0624059 A1 | 11/1994 |

(Continued)

OTHER PUBLICATIONS

Schloss et al., "A statistical toolbox for metagenomics: assessing functional diversity in microbial communities" 9(34) BMC Bioinformatics 1-15 (2008).*

Liu, B. et al. COPE: an accurate k-mer-based pair-end reads connection tool to facilitate genome assembly, Bioinformatics, 28(22); 2870-2874 (Oct. 8, 2012).

Mary, I. et al. Metaproteomic and metagenomic analyses of defined oceanic microbial populations using microwave cell fixation and flow cytometric sorting. FEMS Microbiol Ecol. Oct. 2010;74(1):10-8. doi: 10.1111/j.1574-6941.2010.00927.x. Epub Jul. 5, 2010.

Umbarger, MA. Chromosome conformation capture assays in bacteria. Methods. Nov. 2012;58(3):212-20. doi: 10.1016/j.ymeth. 2012.06.017. Epub Jul. 6, 2012.

Adams, et al. The Genome Sequence of *Drosophila melanogaster*. Science Mar. 24, 2000, 287.5461: 2185-2195 DOI: 10.1126/science. 287.5461.2185.

(Continued)

*Primary Examiner* — Nancy J Leith
(74) *Attorney, Agent, or Firm* — Wilson Sonsini Goodrich & Rosati

(57) ABSTRACT

Disclosed herein are compositions, systems and methods related to sequence assembly, such as nucleic acid sequence assembly of single reads and contigs into larger contigs and scaffolds through the use of read pair sequence information, such as read pair information indicative of nucleic acid sequence phase or physical linkage.

34 Claims, 12 Drawing Sheets

(56) References Cited

U.S. PATENT DOCUMENTS

| | | | |
|---|---|---|---|
| 8,642,295 B2 | 2/2014 | De Laat et al. |
| 8,673,562 B2 | 3/2014 | Drmanac |
| 8,741,577 B2 | 6/2014 | Graneli et al. |
| 2002/0012930 A1 | 1/2002 | Rothberg et al. |
| 2002/0190663 A1 | 12/2002 | Rasmussen |
| 2003/0022207 A1 | 1/2003 | Balasubramanian et al. |
| 2003/0044781 A1 | 3/2003 | Korlach et al. |
| 2003/0064398 A1 | 4/2003 | Barnes |
| 2003/0068629 A1 | 4/2003 | Rothberg et al. |
| 2003/0100102 A1 | 5/2003 | Rothberg et al. |
| 2003/0148344 A1 | 8/2003 | Rothberg et al. |
| 2003/0228627 A1 | 12/2003 | Emerson et al. |
| 2004/0106110 A1 | 6/2004 | Balasubramanian et al. |
| 2004/0197779 A1 | 10/2004 | Apffel |
| 2004/0248161 A1 | 12/2004 | Rothberg et al. |
| 2005/0079510 A1 | 4/2005 | Berka et al. |
| 2005/0100932 A1 | 5/2005 | Lapidus et al. |
| 2005/0124022 A1 | 6/2005 | Srinivasan et al. |
| 2005/0130161 A1 | 6/2005 | Fraser et al. |
| 2005/0260625 A1 | 11/2005 | Wang |
| 2006/0012784 A1 | 1/2006 | Ulmer |
| 2006/0012793 A1 | 1/2006 | Harris |
| 2006/0024678 A1 | 2/2006 | Buzby |
| 2006/0024711 A1 | 2/2006 | Lapidus et al. |
| 2006/0078909 A1 | 4/2006 | Srinivasan et al. |
| 2006/0078937 A1 | 4/2006 | Korlach et al. |
| 2007/0172839 A1 | 7/2007 | Smith et al. |
| 2007/0231817 A1 | 10/2007 | De Laat et al. |
| 2007/0277251 A1 | 11/2007 | Wartiovaara et al. |
| 2009/0111115 A1 | 4/2009 | Drmanac et al. |
| 2009/0191598 A1 | 7/2009 | Ruan et al. |
| 2009/0233291 A1 | 9/2009 | Chen et al. |
| 2009/0269771 A1 | 10/2009 | Schroeder |
| 2009/0298064 A1 | 12/2009 | Batzoglou et al. |
| 2010/0062947 A1 | 3/2010 | De Laat et al. |
| 2010/0081141 A1 | 4/2010 | Chen et al. |
| 2010/0093986 A1 | 4/2010 | Zwick et al. |
| 2010/0130373 A1 | 5/2010 | Dekker et al. |
| 2011/0033854 A1 | 2/2011 | Drmanac et al. |
| 2011/0256593 A1 | 10/2011 | Hsieh et al. |
| 2011/0287947 A1 | 11/2011 | Chen et al. |
| 2011/0300537 A1 | 12/2011 | Slepnev |
| 2011/0306504 A1 | 12/2011 | Xiao et al. |
| 2012/0197533 A1 | 8/2012 | Nazarenko et al. |
| 2012/0302449 A1 | 11/2012 | Dong et al. |
| 2012/0330559 A1 | 12/2012 | Jiang et al. |
| 2013/0005585 A1 | 1/2013 | Anderson et al. |
| 2013/0045872 A1 | 2/2013 | Zhou et al. |
| 2013/0096009 A1 | 4/2013 | Dekker et al. |
| 2013/0183672 A1 | 7/2013 | De Laat et al. |
| 2013/0203605 A1 | 8/2013 | Shendure et al. |
| 2013/0310548 A1 | 11/2013 | Park |
| 2014/0141982 A1 | 5/2014 | Jacobson et al. |
| 2014/0220587 A1 | 8/2014 | Green, Jr. et al. |
| 2015/0363550 A1 | 12/2015 | Green, Jr. et al. |

FOREIGN PATENT DOCUMENTS

| | | |
|---|---|---|
| EP | 0717113 A2 | 6/1996 |
| EP | 0728520 A1 | 8/1996 |
| EP | 1967582 A1 | 9/2008 |
| EP | 2083090 A1 | 7/2009 |
| WO | WO-9015070 A1 | 12/1990 |
| WO | WO-9210092 A1 | 6/1992 |
| WO | WO-9309668 A1 | 5/1993 |
| WO | WO-9511995 A1 | 5/1995 |
| WO | WO-9729212 A1 | 8/1997 |
| WO | WO-9841651 A1 | 9/1998 |
| WO | WO-0014281 A2 | 3/2000 |
| WO | WO-02088382 A2 | 11/2002 |
| WO | WO-02103046 A2 | 12/2002 |
| WO | WO-03020968 A2 | 3/2003 |
| WO | WO-03031947 A2 | 4/2003 |
| WO | WO-2005005655 A1 | 1/2005 |
| WO | WO-2005005657 A1 | 1/2005 |
| WO | WO-2005044836 A2 | 5/2005 |
| WO | WO-2006040550 A1 | 4/2006 |
| WO | WO-2008024473 A2 | 2/2008 |
| WO | WO-2008127281 A2 | 10/2008 |
| WO | WO-2008143903 A2 | 11/2008 |
| WO | WO-2009053039 A1 | 4/2009 |
| WO | WO-2010036323 A1 | 4/2010 |
| WO | WO-2011056872 A2 | 5/2011 |
| WO | WO-2012005595 A2 | 1/2012 |
| WO | WO-2012045012 A2 | 4/2012 |
| WO | WO-2012047726 A1 | 4/2012 |
| WO | WO-2012054873 A2 | 4/2012 |
| WO | WO-2012106546 A2 | 8/2012 |
| WO | WO-2012142531 A2 | 10/2012 |
| WO | WO-2012142611 A2 | 10/2012 |
| WO | WO-2012150317 A1 | 11/2012 |
| WO | WO-2013078470 A2 | 5/2013 |
| WO | WO-2014012010 A1 | 1/2014 |
| WO | WO-2014047561 A1 | 3/2014 |
| WO | WO-2014121091 A1 | 8/2014 |
| WO | WO-2015089243 A1 | 6/2015 |
| WO | WO-2016019360 A1 | 2/2016 |
| WO | WO-2016061517 A2 | 4/2016 |

OTHER PUBLICATIONS

Adey, A. et al. In vitro, long-range sequence information for 19 de novo genome assembly via transposase contiguity. Genome Res., 24(12):2041-2049, Dec. 2014.

Alkan, C. et al. Limitations of next-generation genome sequence assembly. Nat. Methods, 8(1):61-65, Jan. 2011.

Allison 2007 Fundamental Molecular Biology. Wiley-Blackwell, Chapter 8.

Amini, S. et al. Haplotype-resolved whole-genome sequencing by contiguity-preserving transposition and combinatorial indexing. Nat. Genet., 46(12):1343-1349, Dec. 2014.

Ausubel, et al., eds. 1993. Current Protocols in Molecular Biology. Part 1: *E. coli*, plasmids, and bacteriophages.

Blander, G. et al. SIRT1 Shows No Substrate Specificity in Vitro. Journal of biological Chemistry (2005) vol. 280, p. 9780-9785.

Bolger, A.M. et al. Trimmomatic: a flexible trimmer for Illumina sequence data. Bioinformatics, 30(15):2114-2120, Aug. 2014.

Bradnam, K.R. et al. Assemblathon 2: evaluating de novo methods of genome assembly in three vertebrate species. Gigascience, 2(1):10, 2013.

Burton, et al. Chromosome-scale scaffolding of de novo genome assemblies based on chromatin interactions. Nat. Biotechnol. (2013) 31: 1119-1125.

Cai et al. SATB1 packages densely looped transcriptionally active chromatin for coordinated expression of cytokine genes, Nature Genetics, 2006, vol. 38, No. 11, pp. 1278-1288.

Chapman, J.A. et al. Meraculous: de novo genome assembly with short paired-end reads. PLoS One, 6(8):e23501, 2011.

Constans, A. All in the family. The Scientist Magazine 2003, 17.13: 36.

International Application No. PCT/US2014/014184 Search Report and Written Opinion Mailing Apr. 23, 2014.

Cortese, J. The array of today. Scientist. 2000, 14.17: 25.

de Koning, A.P. et al. Repetitive elements may comprise over two-thirds of the human genome. PLoS Genet., 7(12):e1002384, Dec. 2011.

Dekker et al. A closer look at long-range chromosomal interactions. Trends in Biochemical Science 28:277-280 (2003).

Dekker et al. Capturing chromosome conformation Science, 295;1306-1311 (2002).

Dixon, J. R. et al. Topological domains in mammalian genomes identified by analysis of chromatin interactions. Nature, 485(7398):376-380, May 2012.

Dostie et al., Chromosome Conformation Capture Carbon Copy (5C): a massively parallel solution for mapping interaction between genomic elements, Genome research, 2006, vol. 16, No. 10, pp. 1299-1309.

Dower, et al. Recombinant and synthetic randomized peptide libraries. Ann. Rep. Med. Chem. 1991, 26:271-280.

(56) References Cited

OTHER PUBLICATIONS

Drmanac, et al. Human Genome Sequencing Using Unchained Base Reads on Self-Assembling DNA Nanoarrays. Science Jan. 1, 2010, 327.5961: 78-81 DOI:10.1126/science.1181498.

Ekins, R. et al. Microarrays: Their Origins and applications. Trends in Biotechnology, 17(6); 217-218 (Jun. 1999).

Fan et al. A versatile assay for high-throughput gene expression profiling on universal array matrices. Genome Research, 2004, vol. 14 No. 5 pp. 878-885.

Fangman, et al. Activation of replication origins within yeast chromosomes, Annual Review of Cell Biology, 7(1); 375-402 (1991).

Flot, JF et al. Contact genomics: scaffolding and phasing (meta) genomes using chromosome 3D physical signatures. FEBS Letters 589 (2015) 2966-2974.

Fodor, et al. Light-directed, spatially addressable parallel chemical synthesis. Science. Feb. 15, 1991, 251.4995: 767-773; DOI: 10.1126/science.1990438.

Fullwood, et al. ChIP-Based Methods for the Identification of Long-Range Chromatin Interactions Journal of Cellular Biochemistry, vol. 107, No. 1, pp. 30-39, May 2009.

Fullwood, MJ. et al. Chromatin interaction analysis using paired-end tag sequencing. Jan. 2010 Curr. Prot. In Mol. Biol. Chapter 21; unit 21 .15.1-25. doi: 10.1002/0471142727.mb2115s89.

Fyodorov, et al. Chromatin assembly in vitro with purified recombinant ACF and NAP-1. Methods in enzymology. 2002, 371: 499-515.

Garaj, et al. Graphene as a sub-nanometer trans-electrode membrane. Nature. Sep. 9, 2010 467.7312: 190-193. doi: 10.1038/nature09379.

GE Healthcare activated thiol sepharose 4B, Instructions 71-7106-00 AF; Affinity Media, pp. 1-12, (Jul. 2008).

Gilmour, DS et al. Detecting protein-DNA interactions in vivo: distribution of RNA polymerase on specific bacterial genes. Proceedings of the National Academy of Sciences. 1984, 81.14: 4275-4279.

Gnerre, S. et al. High-quality draft assemblies of mammalian genomes from massively parallel sequence data. Proc. Natl. Acad. Sci. U.S.A., 108 (4):1513-1518, Jan. 2011.

Goodwin, S. et al. Oxford nanopore sequencing and de novo assembly of a eukaryotic genome. bioRxiv, Jul. 15, 2015.

Green R. E. et al. Three crocodilian genomes reveal ancestral patterns of evolution among archosaurs. Science, 346(6215):1254449, Dec. 2014.

Grunenwald et al., Rapid, high-throughput library preparation for next-generation sequencing 2010 Nature Methods, vol. 7.

Gwynne, et al. Microarray analysis: the next revolution in molecular biology. Science. Aug. 6, 1999.

Haussler, D., et al. Genome 10K: a proposal to obtain whole-genome sequence for 10,000 vertebrate species. J. Hered., 100(6):659-674, 2009.

Heid, et al. Real time quantitative PCR. Genome research. 1996: 6.10: 986-994.

Herschleb, et al. Pulsed-field gel electrophoresis. Pulsed-field gel electrophoresis. Nat Protoc. 2007, 2.3: 677-84.

International Human Genome Sequencing Consortium. Finishing the euchromatic sequence of the human genome. Nature, 431(7011):931-945, Oct. 2004.

Kalhor, R., et al. Genome architectures revealed by tethered chromosome conformation capture and population-based modeling. Nat. Biotechnol., 30(1):90-98, Jan. 2012.

Kaplan, N. et al. High-throughput genome scaffolding from in vivo DNA interaction frequency. Nat. Biotechnol., 31(12):1143-1147, Dec. 2013.

Kidd, J. M. et al. Mapping and sequencing of structural variation from eight human genomes. Nature, 453(7191):56-64, May 2008.

Kitzman et al., Haplotype-resolved genome sequencing of Gujarati Indian Individual, Nature Biotechnology, 2011, vol. 29, No. 1, pp. 59-63.

Koren, S. et al. Hybrid error correction and de novo assembly of single-molecule sequencing reads. Nature biotechnology, 30(7):693-700, 2012.

Kotoulas, et al. The chipping forecast. Special supplement to Nature Genetics vol. 21 (1999).

Kundu et al. Activator-dependent transcription from chromatin in vitro involving targeted histone acetylation by p300. Molecular cell. 2000, 6.3: 551-561.

Lasken, et al. Mechanism of chimera formation during the Multiple Displacement Amplification reaction. BMC biotechnology. 7(1): 19 (2007).

Lee, TI et al. Chromatin immunoprecipitation and microarray-based analysis of protein location, Nature Protocols 1(2) : 729-748 (2006).

Lemieux, et al. Overview of DNA chip technology. Molecular Breeding. 1998, 4.4: 277-289.

Levene, et al. Zero-Mode Waveguides for Single-Molecule Analysis at High Concentrations. Science. Jan. 31, 2003, 299.5607: 682-686; DOI: 10.1126/science.1079700.

Lieberman-Aiden, et al. Comprehensive mapping of long range interactions reveals folding principles of the human genome. Science. Oct. 9, 2009; 326(5950): 289-293. doi:10.1126/science. 1181369.

Lupski, et al. Whole-genome sequencing in a patient with Charcot-Marie-Tooth neuropathy. New England Journal of Medicine. 2010, 362.13: 1181-1191.

Lusser, A. et al. Strategies for the reconstitution of chromatin. Nature Methods. 1(1): 19-26 (2004).

Ma, et al. Application of Real-time Polymerase Chain Reaction (RT-PCR). The Journal of American Science. 2(3);1-19 (2006).

Maniatis, et al. Molecular Cloning: A Laboratory Manual, Cold Spring Harbor, N.Y., pp. 280-281 (1982).

Margulies, et al. Genome Sequencing in Open Microfabricated High Density Picoliter Reactors. Nature. Sep. 15, 2005; 437.7057: 376-380.

Marie-Nelly, H. et al. High-quality genome (re)assembly using chromosomal contact data. Nat Commun, 5:5695, 2014.

Marshall, et al. DNA chips: an array of possibilities. Nat Biotechnol. Jan. 1998, 16.1: 27-31.

Meyer, M. et al. Illumina sequencing library preparation for highly multiplexed target capture and sequencing. Cold Spring Harb Protoc, 2010(6):pdb.prot5448, Jun. 2010.

Miller et al. A Simple salting out procedure for extracting DNA from human nucleated cells. Nucleic Acids Research vol. 16, No. 3, 1215 (1988).

Morrison, AJ et al. Retinoblastoma Protein Transcriptional Repression through Histone Deacetylation of a Single Nucleosome. Molecular and Cellular biology (2002) vol. 22, p. 856-865.

Myers, EW et al. A whole-genome assembly of *Drosophila*. Science (2000) 287(5461); 2196-2204.

Nazarenko, et al. A closed tube format for amplification and detection of DNA based on energy transfer. Nucleic acids research. 1997, 25.12: 2516-2521.

Peng et al., Generation of long insert pairs using a Cre-LoxP Inverse PCR approach, PLoS One, 2012, vol. 7, No. 1, p. e29437.

Peters et al., Accurate whole-genome sequencing and haplotyping from 10 to 20 human cells, Nature, Jul. 12, 2012, vol. 487, pp. 190-195.

Putnam, N.H. et al. Chromosome-scale shotgun assembly using an in vitro method for long-range linkage. arXiv:1502.05331[q-bio. GN] pp. 1-25. Feb. 18, 2015 (Retrieved from the Internet Oct. 8, 2015).

Quail, M. A. et al. A tale of three next generation sequencing platforms: comparison of Ion Torrent, Pacific Biosciences and Illumina MiSeq sequencers. BMC Genomics, 13:341, 2012.

Rios, et al. Identification by whole-genome resequencing of gene defect responsible for severe hypercholesterolemia. Human molecular genetics. 2010, 19.22: 4313-4318.

Rozowsky, J. et al. AlleleSeq: analysis of allele-specific expression and binding in a network framework. Mol. Syst. Biol., 7:522, 2011r.

Salzberg, S. L. et al. GAGE: A critical evaluation of genome assemblies and assembly algorithms. Genome Res., 22(3):557-567, Mar. 2012.

(56) References Cited

OTHER PUBLICATIONS

Sambrook, et al. Mixed Oligonucleotide-primed Amplification of cDNA (MOPAC). Cold Spring Harbor Protocols. 2006.1: pdb-prot3484.
Schena, et al. Genes, genomes, and chips. DNA microarrays: A practical approach. 1999: 1-15.
Schena, et al. Parallel analysis with biological chips. PCR applications: protocols for functional genomics. 1999 445-456.
Schena, M. Microarray Biochip Technology (2000).
Schmidt, D. et al. ChIP-seq: using high-throughput sequencing to discover protein-DNA interactions. Methods (2009) vol. 48, pp. 240-248.
Schwartz, et al. Separation of yeast chromosome-sized DNAs by pulsed field gradient gel electrophoresis. Cellshi 1984, 37.1: 67-75.
Selvaraj, et al. Whole-genome haplotype reconstruction using proximity-ligation and shotgun sequencing. Nat. Biotechnol. 2013, 31: 1113-1119.
Selvaraj, Siddarth et al. Complete haplotype phasing of the MHC and KIR loci with targeted HaploSeq BMC Genomic 16:900, pp. 1-7 (2015).
Selvaraj, S. et al. Whole-genome haplotype reconstruction using proximity-ligation and shotgun sequencing. Nat. Biotechnol., 31(12):1111-1118, Dec. 2013.
Shalon, et al. A DNA microarray system for analyzing complex DNA samples using two-color fluorescent probe hybridization. Genome research. 1996, 6.7: 639-645.
Shedlock, A. M.et al. Phylogenomics of nonavian reptiles and the structure of the ancestral amniote genome. Proc. Natl. Acad. Sci. U.S.A., 104(8):2767-2772, Feb. 2007.
Sheridan, C. Milestone approval lifts Illumina's NGS from research into clinic. Nat. Biotechnol., 32 (2):111-112, Feb. 2014.
Shiio Y., et al. Quantitative proteome analysis using isotope-coded affinity tags and mass spectrometry et al. Nature Protocols 1(1); 139-145 (2006).
SIGMA Protein A immobilized product sheet (03/01). (Accessed on Apr. 14, 2016).
Simpson, J. T. et al. Durbin. Efficient de novo assembly of large genomes using compressed data structures. Genome Res., 22(3):549-556, Mar. 2012.
Solomon, Mark J., et al. Formaldehyde-mediated DNA-protein crosslinking: a probe for in vivo chromatin structures. Proceedings of the National Academy of Sciences. 1985, 82.19: 6470-6474.
Solomon MJ, et al. A. Mapping protein-DNA interactions in vivo with formaldehyde: svidence that histone H4 is retained on a highly transcribed gene. Cell. 1988, 53(6):937-947.
Soni, et al. Progress toward ultrafast DNA sequencing using solid-state nanopores. Clin Chem. Nov. 2007, 53.11: 1996-2001. Epub Sep. 21, 2007.
Splinter, E. 3C Technology: Analyzing the Spatial Organization of Genomic Loci In Vivo Methods in Enzymology, vol. 375, pp. 493-507, 2003.
Syed Optimized library preparation method for next-generation sequencing. Nature Methods, Oct. 2009.
Tanizawa et al., Mapping of long-range associations throughout the fission yeast genome reveals global genome organization linked to transcriptional regulation. Nucleic Acid Research, 2010, vol. 38, pp. 8164-8177.
Teague, et al. High-resolution human genome structure by single-molecule analysis. Proceedings of the National Academy of Sciences. 2010, 107.24: 10848-10853.
Torjensen, I. Genomes of 100,000 people will be sequenced to create an open access research resource. BMJ, 347:f6690, 2013.
Tuzun, E. et al. Fine-scale structural variation of the human genome. Nat. Genet., 37(7):727-732, Jul. 2005.
Tyagi, et al. Molecular beacons: probes that fluoresce upon hybridization. Nature biotechnology. 1996, 14.3: 303-308.
U.S. Appl. No. 14/170,339 Non-Final Office Action Mailed Oct. 20, 2014.
U.S. Appl. No. 14/170,339 Restriction Requirement Dated Mar. 14, 2014.
Venter, et al. The sequence of the human genome. Science. Feb. 16, 2001 291.5507:1304-51.
Voskoboynik, A. et al. The genome sequence of the colonial chordate, Botryllus schlosseri. Elife, 2:e00569, 2013.
Weisenfeld N.I., et al. Comprehensive variation discovery in single human genomes. Nat Genet 46: 1350-1355 (Dec. 2014).
Whitcombe, et al. Detection of PCR Products Using Self-probing Amplicons and Fluorescence. Nature Biotechnology. 1999, 17:804-807.
Williams, L. J. Paired-end sequencing of Fosmid libraries by Illumina. Genome Res., 22(11):2241-2249, Nov. 2012.
Wing, et al. An improved method of plant megabase DNA isolation in agarose microbeads suitable for physical mapping and YAC cloning. The Plant Journal. 1993, 4.5: 893-898.
Wu, T.D. et al. GMAP: a genomic mapping and alignment program for mRNA and EST sequences. Bioinformatics, 21(9):1859-1875, May 2005.
Wu, C.C. et al. Long-span, mate-pair scaffolding and other methods for faster next-generation sequencing library creation. Nat. Methods, 9(9; Advertising Feature):i-ii, Sep. 2012.
Zhou, et al. A single molecule scaffold for the maize genome. PLoS Genetics. 2009, 5.11: e1000711.
Zinchenko, A. et al. Compaction of Single-Chain DNA by Histone-Inspired Nanoparticles. Physical Review Letters, 95(22); 228101 (2005).
Hesselberth, Jay R. et al. Global mapping of protein-DNA interaction in vivo by digital genomic footprinting, Nature Methods 6(4): 283-289 (Apr. 2009).
International Application No. PCT/US2016/018295 International Search Report Issued Aug. 4, 2016.
International Application No. PCT/US2016/024225 International Search Report Issued Jul. 10, 2016.
Nickitas-Etienne, Athina International Preliminary Report on Patentability and Written Opinion, PCT/US2014/069642, The International Bureau of WIPO, Jun. 23, 2016.
Putnam, N. H. et al. Supplemental Material—Chromosome-scale shotgun assembly using an in vitro method for long-range likage, Genome Research 26:342-350 (2016).
Storek, Michael J. et al. High-resolution footprinting of sequence-specific protein-DNA contacts, Nature Biotechnology, 20(2):183-186 (Feb. 1, 2002).

* cited by examiner

NUCLEIC ACID SEQUENCE ASSEMBLY

CROSS-REFERENCE

This application claims the benefit of U.S. Provisional Application No. 62/117,256, filed Feb. 17, 2015, which is hereby explicitly incorporated by reference in its entirety, and this application also claims the benefit of U.S. Provisional Application No. 62/294,208, filed Feb. 11, 2016, which is hereby explicitly incorporated by reference in its entirety.

STATEMENT AS TO FEDERALLY SPONSORED RESEARCH

This invention was made with government support under contract number 5R44HG008719-02 awarded by the National Institutes of Health. The government has certain rights in the invention.

BACKGROUND

Currently accessible and affordable high-throughput sequencing methods are best suited to the characterization of short-range sequence contiguity and genomic variation. Achieving long-range linkage and haplotype phasing requires either the ability to directly and accurately read long (e.g., tens of kilobases) sequences, or the capture of linkage and phase relationships through paired or grouped sequence reads. However, grouping sequencing information and generating an assembly of the sequence information necessary to achieve long-range linkage and haplotype phasing is computationally intensive and time consuming. Disclosed herein are computationally efficient methods and systems to obtain assemblies with chromosome-scale contiguity from sequence information informed by paired or grouped sequence reads.

SUMMARY

Disclosed herein are methods, compositions, algorithms, and systems related to the scaffolding of nucleic acid data. Approaches herein utilize read pairs to infer information regarding the phase or physical linkage information of contigs to which the reads of a read pair map in a dataset. Contigs in a nucleic acid dataset are ordered, oriented or merged end to end or in some cases inserted one into another (collectively "scaffolded") in light of the impact of such activity on a score or parameter relating to their relative positioning.

In some cases the score or parameter is a measure of the resulting impact of contig repositioning on aggregate read pair separation for a read pair dataset of one or another contig configuration. Depending on the approach used to generate it, a dataset of read pairs may have a particular read pair separation distribution curve. Mapped as read pair separation as a function of frequency, one can determine an expected read pair distance distribution for a given read pair dataset. One may then map the read pairs to a set of contigs, and position the contigs (in order, orientation or otherwise) so as to make the read pair distance distribution for the data set match, approximate, or more closely approximate the read pair distance distribution expected given a nucleic acid sample and a method of read pair generation.

Contig positioning variously involves ordering contigs or scaffolds relative to one another, orienting contigs or scaffolds relative to one another, joining contigs or scaffolds end-to-end, inserting one or more contigs into a gap in a contig or scaffold of contigs, or splitting a contig or scaffold that is misassembled in a data set. In some cases this process is continued until an optimal or optimized configuration is obtained, while in alternate cases the process is practiced only to achieve an improvement over an initial contig or scaffold configuration. Alternately, the process is continued until some fraction of the sample contig set is correctly scaffolded, for example 70%, 75%, 80%, 85% 90% 95%, 99% or 99.9% or more. In many cases sequence datasets representative of even complex genomic samples such as human or polyploid plant sample genomes or transposon rich genomic samples, computational assessment of dataset configuration and dataset improvement by contig ordering, orientation, combining end to end, combining of one scaffold within another, or breaking a scaffold or contig (collectively "scaffolding") is completed in no more than 8 hours, 7 hours, six hours, five hours, four hours or fewer than four hours.

The score assessment is made either globally or locally or both globally and locally, by examining a subset of adjacent contigs or scaffolds at a time. When performed locally, a subset of, for example, 2, 3, 4, 5, 6 or more than six contigs are examined to determine an optimized score, and then the 'window' is shifted one contig and the process repeated, often in light of the optimized configuration determined for the previous window. Alternately, subsets are defined as fractions of the total nucleic acid sequence set (e.g., a genome or plurality of genomes), such as 0.01%, 0.1%, 1%, or 5% at a time. In some cases the 'window' size will vary, such that easily assembled regions are assigned large windows, while more challenging regions, or regions with a higher density of reads or a higher density of reads that are contradictory, complicating analysis, are assigned a smaller window size.

Provided herein are methods for scaffolding contigs of nucleic acid sequence information comprising obtaining a set of contig sequences having an initial configuration; obtaining a set of paired end reads; obtaining standard paired-end read distance frequency data; grouping contig pairs sharing sequence that coexists in at least one paired end read; and scaffolding the grouped contig sequences such that read pair distance frequency data for read pairs that map to separate contigs more closely approximates the standard paired-end read distance frequency data relative to the read pair frequency data of the contig sequences in the initial configuration. The scaffolding comprises at least one of ordering the set of contigs, orienting the set of contigs, merging at least two contigs end to end, inserting one contig into a second contig and cleaving a contig into at least two constituent contigs. In some methods, standard paired-end read frequency is obtained from paired-end reads where both reads map to a common contig. Alternately or in combination, standard paired-end read frequency is obtained from previously generated curves. The initial configuration is a random configuration, or is preconfigured. In preferred embodiments, read pair distance frequency data for read pairs that map to separate contigs more closely approximates the paired-end read distance frequency data when read pair distance likelihood increases. In many cases, read-pair distance likelihood is maximized. Read pair distance frequency data for read pairs that map to separate contigs more closely approximates the paired-end read distance frequency data when a statistical measure of difference between the read pair distance frequency data and the standard paired-end read distance frequency data decreases. A number of statistical measures are available. For example, statistical measure of distance between the read pair distance frequency data and the standard paired-end read distance frequency data comprises at least one of ANOVA, a t-test, and a X-squared test in various cases. Read pair distance for read pairs that map to separate contigs more closely matches the paired-end read distance frequency data when deviation of read pair distance distribution among ordered contigs obtained as compared to standard paired-end read distance frequency decreases. Alternately or in combination, deviation of read pair distance distribution among ordered contigs obtained as compared to standard paired-end read distance frequency is minimized. In some scaffold assessment, a contig that shares sequence in a paired end read associated with a first cluster and a second cluster is assigned to a cluster having a greater number of shared end reads. Clustering often comprises placing contigs into a number of groups that is greater than or equal to the number of chromosomes in the organism. Often, a contig sharing only a single paired end read with one contig of a cluster is not included in that cluster. A contig sharing with a cluster only at least one paired end read comprising repetitive sequence is often not included in that cluster. Similarly, a contig sharing with a cluster only at least one paired end read comprising low quality sequence is often not included in that cluster. In some methods the set of paired-end reads are obtained by digesting sample DNA to generate internal double strand breaks within the nucleic acid, allowing the double strand breaks to re-ligate to form at least one religation junction, and sequencing across at least one religation junction. The DNA is crosslinked to at least one DNA binding agent, such as a nuclear protein or a nanoparticle, in some approaches to paired read generation. The DNA is isolated naked DNA that is reassembled into reconstituted chromatin, although DNA having binding proteins is suitable under some circumstances, particularly if DNA molecules are not bound to one another. Often, the reconstituted chromatin is crosslinked. The reconstituted chromatin comprises a DNA binding protein. Alternately or in combination, the reconstituted chromatin comprises a nanoparticle. Preferably in some cases, clustering of contigs is independent of the number or chromosomes for the organism. A contig that shares sequence in a paired end read associated with a first cluster and a second cluster is assigned to a cluster having a greater number of shared end reads in many cases. Alternately or in combination, a contig that shares sequence in a paired end read associated with a first cluster and a second cluster is assigned to a cluster having a greater read pair distance likelihood value, or a contig that shares sequence in a paired end read associated with a first cluster and a second cluster is assigned to a cluster having a lower deviation in its read pair distribution relative to a standard read pair distance distribution. Alternately, a contig that shares sequence in a paired end read associated with a first cluster and a second cluster is excluded from each cluster. Often, clustering comprises placing contigs into a number of groups that is greater than or equal to the number of chromosomes in the organism. Some scaffolding comprises selecting a first set of putative adjacent contigs of said clustered contigs, determining a minimal distance order of said first set of putative adjacent contigs that reduces an aggregate measure of the read-pair distances for said read pairs, and scaffolding said first set of putative adjacent contigs so as to reduce said aggregate measure of the read-pair distance. The first set of putative adjacent contigs consists of 2 contigs. Alternately, the first set of putative adjacent contigs consists of 3 contigs. Alternately, the first set of putative adjacent contigs consists of 4 contigs. Alternately, the first set of putative adjacent contigs comprises 4 contigs. Some scaffolding comprises determining an order and an orientation of each contig in said first set of putative adjacent contigs. Determining a minimal distance order comprises comparing the expected read-pair distance for at least one read pair that comprises reads mapping to two contigs of said set for all possible contig configurations in some cases. Scaffolding often comprises selecting the contig orientation that corresponds to the minimal read-pair distance for said read pair. Some methods further comprise selecting the contig orientation that corresponds to the maximum likelihood read pair distance distribution. Some methods further comprise selecting the contig orientation that corresponds to the minimal read-pair distance for an aggregate measure of read pairs of said contig cluster. In some methods, the expected read-pair distance is compared to said paired-end read distance frequency data. In some methods, the comparing to said paired-end read distance frequency data comprises using Formula 1. Some methods comprise selecting a second set of putative adjacent contigs of said clustered contigs, said second set comprising all but one end-terminal contig of said first set, and comprising one additional contig of said clustered contigs, and scaffolding said second set of putative adjacent contigs so as to reduce said aggregate measure of the read-pair distance. Some methods comprise selecting a third set of putative adjacent contigs of said clustered contigs, said third set comprising all but one end-terminal contig of said second set, and comprising one additional contig of said clustered contigs not included in said first set and not included in said second set, and scaffolding said third set of putative adjacent contigs so as to reduce said aggregate measure of the read-pair distance. This is followed in many cases by iteratively selecting at least one additional set until a majority of said clustered contigs are ordered. Selecting often involves iteratively selecting at least one additional set until each of said clustered contigs are ordered. The nucleic acid sequence is derived from a sample such as a genome, or in some cases, a plurality of genomes. In some embodiments, the methods are practiced on a computer-implemented system comprising a processor configured to receive contig and read pair data as discussed herein, process the data as discussed above, and output scaffolded contig data having the improved parameters as discussed above.

Provided herein are methods for scaffolding contigs in a cluster, comprising: assigning a log-likelihood ratio score for each pair of contigs; sorting connections by ratio score; and accepting or rejecting contig connections in decreasing order of ratio score so as to increase the total score of the assembly. In some methods, the scaffolding comprises ordering the set of contigs, and/or orienting the set of contigs, and/or merging at least two contigs end to end, and/or inserting one contig into a second contig, and/or cleaving a contig into at least two constituent contigs. In many cases, the contigs comprise a genome, or a plurality of genomes. In some embodiments, the methods are practiced on a computer-implemented system comprising a processor configured to receive contig and read pair data as discussed herein, process the data as discussed above, and output scaffolded contig data having the improved parameters as discussed above.

Provided herein are methods for determining locally optimal contig configuration of a plurality of contigs within a cluster. Some such methods comprise a) identifying a sequence window of size w contigs starting at position i along a cluster of contigs; b) considering $w! \, 2^w$ ordering and orienting options for the contigs of window w by examining the scores of compatible orders and orientations in each position i in the window; c) orienting and ordering said w contigs in said window to obtain an optimal score; d) shifting the window to position i+1; and e) repeating steps (a), (b) and (c) for said window at position i+1 using the orienting and ordering of said w contigs to determine and optimal score; thereby orienting and ordering said plurality of contigs in a locally optimal configuration relative to the score. In some methods, read pair data mapping to the plurality of contigs in the cluster is obtained, a standard paired-end read frequency data set is obtained, and the score for an orienting and ordering of said w contigs is a measure of how closely a read pair distance data set for the read pair data mapping to the plurality of contigs in the cluster matches the standard paired-end read frequency data set. In some methods, read pair data mapping to the plurality of contigs in the cluster is obtained, the score is total read pair distance, and the score is optimized when total read pair distance is minimized. The window size w is 3, or alternately w is 4, or alternately w is 5, or alternately w is 6. In some cases w has a first value for a first cluster and w has a second value at a second cluster. w is selected in some methods to comprise 1% of the contigs of the set, or alternately 5% of the contigs of the set, or alternately 10% of the contigs of the set. In many methods the score is a read pair distance likelihood score, and the score is optimal when the score is maximized for a given window size. The score is calculated using formula 1 in some exemplary embodiments. The score is a deviation from an expected read pair distribution, and is optimal when the score is minimized for a given window size in some cases. The plurality of contigs comprises a genome, or a plurality of genomes, or a non-genomic nucleic acid source. In some embodiments, the methods are practiced on a computer-implemented system comprising a processor configured to receive contig and read pair data as discussed herein, process the data as discussed above, and output scaffolded contig data having the improved parameters as discussed above.

Provided herein are methods for nucleic acid sequence assembly, comprising: obtaining purified DNA; binding the purified DNA with a DNA binding agent to form DNA/chromatin complexes; incubating the DNA-chromatin complexes with restriction enzymes to leave sticky ends; performing ligation to join ends of DNA; sequencing across ligated DNA junctions to generate paired end reads; and using the paired end reads to scaffold a nucleic acid data set comprising contigs representing sequence of the purified DNA. In some methods the purified DNA is derived from a genome, or from a plurality of genomes. In some embodiments, the methods are practiced on a computer-implemented system comprising a processor configured to receive contig and read pair data as discussed herein, process the data as discussed above, and output scaffolded contig data having the improved parameters as discussed above.

Provided herein are methods for identifying a read-paired sequence read mapping to a repetitive contig region, comprising: obtaining a contig dataset for a nucleic acid sample; obtaining at least one read-paired sequence read corresponding to nonadjacent physically linked sequence information; and excluding the read-paired sequence read if at least one read of the read paired sequence read maps to two distinct loci of a contig data set. In some methods the repetitive region comprises sequence having a shotgun read depth exceeding a first threshold. In some methods the repetitive region comprises a base position having a read depth exceeding a second threshold. Often, the first threshold and second threshold are fixed relative to the overall distribution of read depth. The first threshold is 3 times the overall distribution of read depth in many cases. Alternately, the first threshold is 2, 2.5, 3.5, 4, 4.5, 5, 5.5, 6, or a non-integer value within or adjacent to this set. The second threshold is often 3.5 times the overall distribution of read depth. Alternately, the second threshold is 2, 2.5, 3, 4, 4.5, 5, 5.5, 6, or a non-integer value within or adjacent to this set. In some methods the purified DNA is derived from a genome, or from a plurality of genomes. In some embodiments, the methods are practiced on a computer-implemented system comprising a processor configured to receive contig and read pair data as discussed herein, process the data as discussed above, and output scaffolded contig data having the improved parameters as discussed above.

Provided herein are methods for guiding contig assembly decisions, comprising the step of determining the probability of observing the number and implied separations of spanning read-paired sequence between a first contig and a second contig, wherein the contigs have relative orientations of o within the set [++, +−, −+, −−] and are separated by a gap length. Some methods further comprise normalizing the probability of distribution of read-pair sequence over separation distances, wherein normalizing includes comparing the read-pair sequence to noise pairs which sample the nucleic acid sample independently. In some cases the nucleic acid sample comprises a genome. Alternately, the nucleic acid sample comprises a plurality of genomes, or a non-genomic source. Often, the total number of noise pair is determined by tabulating the densities of links for a sample of contig pairs. Further provided herein are methods wherein the highest and lowest 1% of densities are excluded. In alternatives thereto, the highest 0.5%, 0.6%, 0.7%, 0.8%, 0.9%, 1.1%, 1.2%, 1.3%, 1.4%, 1.5%, 1.6%, 1.7%, 1.8%, 1.9%, 2%, 3%, 4%, 5%, or greater than 5% are excluded, and similarly the lowest 0.5%, 0.6%, 0.7%, 0.8%, 0.9%, 1.1%, 1.2%, 1.3%, 1.4%, 1.5%, 1.6%, 1.7%, 1.8%, 1.9%, 2%, 3%, 4%, 5%, or greater than 5% are excluded. Some methods comprise determining contig order. Some methods comprise determining contig orientation. Some methods comprise determining both contig order and contig orientation. In some embodiments, the methods are practiced on a computer-implemented system comprising a processor configured to receive contig and read pair data as discussed herein, process the data as discussed above, and output scaffolded contig data having the improved parameters as discussed above.

Provided herein are methods for contig misjoin correction comprising obtaining a set of contig sequences having an initial configuration; obtaining a set of paired end reads; obtaining standard paired-end read distance frequency data; grouping contig pairs sharing sequence that coexists in at least one paired end read; comparing read pair frequency data for the grouping of the contigs to the standard paired-end read distance frequency data; determining whether introducing a break in a contig of the grouping causes the read pair frequency data for the grouping of the contigs to more closely approximate the standard paired-end read distance frequency data; and, if the read pair frequency data for the grouping of the contigs to more closely approximate the standard paired-end read distance frequency data, then introducing a break into the contig. In some methods the first position is merged with at least one adjacent second position having said log likelihood below said threshold prior to introducing the break. The second adjacent position is no greater than 300 bases pairs from the first position. Alternately, the second position does not include positions greater than 1000 base pairs from the first position. Alternately, the second adjacent position is no greater than 50, 100, 150, 200, 250, 350, 400, 450, 500, 550, 600, 650, 700, 750, 800, 850, 900, 950, 1100, 1200, 1300, 1400, 1500, 1600, 1700, 1800 1900, or 2000, or an integer value within the range spanned by the values recited. Further provided herein are methods wherein determining the log likelihood change comprises identifying an average paired end mapping density for a contig, identifying segments of the contig having a paired end mapping density of at least 3× that of the average paired end mapping density, and excluding segments of the contig having a paired end mapping density of at least 3× that of the average paired end mapping density. Alternately, a threshold of 1.5×, 1.6×, 1.7×, 1.8×, 1.9×, 2.0×, 2.1×, 2.2×, 2.3×, 2.4×, 2.5×, 2.6×, 2.7×, 2.8×, 2.9×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7, 4.8×, 4.9×, 5× or greater than 5× is used. Further provided herein are methods wherein the set of contig sequences is derived from a genome. Further provided herein are methods wherein the set of contig sequences is derived from a plurality of genomes. In some embodiments, the methods are practiced on a computer-implemented system comprising a processor configured to receive contig and read pair data as discussed herein, process the data as discussed above, and output scaffolded contig data having the improved parameters as discussed above.

Provided herein are methods for contig assembly, comprising: indicating broken contigs of the starting assembly, wherein broken contigs are nodes and edges of the broken contigs are labeled with a list of ordered pairs of integers and wherein the edges of the breaks correspond to mapped read-paired sequence; and excluding edges with fewer than a threshold number of mapped connections. In some methods the threshold number is less than 5%. Alternately, the number is less than 20%, 15%, 14%, 13%, 12%, 11%, 10%, 9%, 8%, 7%, 6%, 4%, 3%, 2%, 1% or lower. In some cases the threshold number is fewer than $t_L$ links. In some methods contigs comprise edges where the ratio of the degree in the graph of a corresponding node to contig length is base pairs exceeds about 5% of high end of the distribution all values. In some methods the contigs are derived from a genome. In some methods the contigs are derived from a plurality of genomes. In some embodiments, the methods are practiced on a computer-implemented system comprising a processor configured to receive contig and read pair data as discussed herein, process the data as discussed above, and output scaffolded contig data having the improved parameters as discussed above.

Provided herein are methods of assembling contig sequence information into at least one scaffold, comprising obtaining sequence information corresponding to a plurality of contigs, obtaining paired-end read information from a nucleic acid sample represented by the plurality of contigs, and configuring the plurality of contigs such that deviation of a read pair distance parameter from a predicted read pair distance data set is minimized, wherein the configuring occurs in less than 8 hours. The predicted read pair distance data set comprises a read pair distance likelihood curve in many preferred embodiments. In some cases the read pair distance parameter is maximum distance likelihood relative to a read pair distance likelihood curve. Alternately, the read pair distance parameter is minimum variation relative to a read pair distance likelihood curve. The locally adjacent set of contigs comprises 2 contigs. Alternately, the locally adjacent set of contigs comprises 3 contigs. Alternately, the locally adjacent set of contigs comprises 4 contigs. Alternately, the locally adjacent set of contigs comprises 5 contigs. Alternately, the locally adjacent set of contigs comprises 6 contigs. Preferably, the configuring occurs in less than 7 hours. Alternately, the configuring occurs in less than 6 hours, 5 hours, 4 hours, 3 hours, 2 hours, 1 hour, or less than 1 hour. The contig information is derived from a genome in many cases. Alternately, the contig sequence information is derived from a plurality of genomes. In some embodiments, the methods are practiced on a computer-implemented system comprising a processor configured to receive contig and read pair data as discussed herein, process the data as discussed above, and output scaffolded contig data having the improved parameters as discussed above.

Provided herein are methods of scaffolding a set of contig sequences comprising obtaining a set of contig sequences representative of a nucleic acid sample obtaining read pair data for the nucleic acid sample, and ordering and orienting the set of contig sequences such that read pair data for the nucleic acid sample more closely approximates an expected read pair distribution, wherein 70% of the set of contig sequences are ordered and oriented so as to match the relative order and orientation of their sequences in the nucleic acid sample in no more than 8 hours. The scaffolding comprises at least one of ordering the set of contigs, orienting the set of contigs, merging at least two contigs end to end, inserting one contig into a second contig, and/or cleaving a contig into at least two constituent contigs. In some methods, 80% of the set of contig sequences are ordered and oriented so as to match the relative order and orientation of their sequences in the nucleic acid sample in no more than 8 hours. Alternately, 90% of the set of contig sequences are ordered and oriented so as to match the relative order and orientation of their sequences in the nucleic acid sample in no more than 8 hours. Alternately, 95% of the set of contig sequences are ordered and oriented so as to match the relative order and orientation of their sequences in the nucleic acid sample in no more than 8 hours. In some cases, 70% of the set of contig sequences are ordered and oriented so as to match the relative order and orientation of their sequences in the nucleic acid sample in no more than 4 hours, or alternately in no more than 2 hours. or alternately in no more than 1 hour. The contig information is derived from a genome in many cases. Alternately, the contig sequence information is derived from a plurality of genomes.

Provided herein are methods of configuring a set of nucleic acid sequence data comprising: obtaining sequence information corresponding to a plurality of contigs which comprise the scaffold, obtaining pair-end read information, and configuring the plurality of contigs such that paired-end read distance distribution for the paired-end read information is globally optimized to approximate a reference paired-end read distance distribution, wherein the configuring occurs in less than 8 hours. The contig information is derived from a genome in many cases. Alternately, the contig sequence information is derived from a plurality of genomes. In some embodiments, the methods are practiced on a computer-implemented system comprising a processor configured to receive contig and read pair data as discussed herein, process the data as discussed above, and output scaffolded contig data having the improved parameters as discussed above.

Provided herein are methods of improving a scaffold assembly comprising obtaining a scaffold set comprising a plurality of joined nodepairs, wherein each node of a node pair comprises at least one contig sequence, obtaining pair-end read information mapped to the plurality of joined nodes, counting the number of read pairs shared by a joined nodepair, comparing said number to a threshold, and cleaving a node pair into unjoined nodes if said number falls below a threshold. In some cases only read pairs mapping to unique contig sequence are counted. Further provided herein are methods wherein read pairs mapping to a contig sequence segment to which a threshold number of distinct reap pair ends map are discarded. The threshold number is 3× the average number for non-repetitive sequence in many cases. Alternately, threshold values of 1.5×, 1.6×, 1.7×, 1.8×, 1.9×, 2×, 2.1×, 2.2×, 2.3×, 2.4×, 2.5×, 2.6×, 2.7×, 2.7×, 2.8×, 2.9×, 3.1×, 3.2×, 3.3×, 3.4×, 3.5×, 3.6×, 2.7×, 2.8×, 3.9×, 4×, 4.5×, 5× or greater than 5× are employed. The contig information is derived from a genome in many cases. Alternately, the contig sequence information is derived from a plurality of genomes. In some embodiments, the methods are practiced on a computer-implemented system comprising a processor configured to receive contig and read pair data as discussed herein, process the data as discussed above, and output scaffolded contig data having the improved parameters as discussed above.

Provided herein are methods of improving a scaffold assembly comprising obtaining a scaffold set comprising a plurality of joined nodepairs, wherein each node of a node pair comprises at least one contig sequence, obtaining pair-end read information mapped to the plurality of joined nodes, obtaining standard paired-end read distance frequency data; comparing pair-end read frequency data for the paired end read information mapped to the plurality of joined nodes to the standard paired-end read distance frequency data; and cleaving at least one joined node if cleaving the joined node results in pair-end read frequency data for the paired end read information mapped to the plurality of joined nodes to more closely approximate the standard paired-end read distance frequency data. The contig information is derived from a genome in many cases. Alternately, the contig sequence information is derived from a plurality of genomes. In some embodiments, the methods are practiced on a computer-implemented system comprising a processor configured to receive contig and read pair data as discussed herein, process the data as discussed above, and output scaffolded contig data having the improved parameters as discussed above.

Provided herein are methods of scaffold assembly comprising obtaining a set of contig sequences obtaining input data comprising a set of paired end reads, wherein at least 1% of the paired end reads comprise a read pair distance of at least 1 kb, wherein the set of paired end reads comprises paired end reads in a natural orientation, wherein the sequencing error rate for the read pairs is no greater than 0.1%, and wherein the RN50 of the input data is no greater than 20% of the assembled scaffold, and outputting a scaffold, wherein the RN50 for the scaffold is at least 2× the RN50 of the input. Optionally, the error rare is no greater than 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.001%, 0.0001%, or 0.00001% or less. In some embodiments, the methods are practiced on a computer-implemented system comprising a processor configured to receive contig and read pair data as discussed herein, process the data as discussed above, and output scaffolded contig data having the improved parameters as discussed above.

Provided herein are methods of scaffold assembly comprising: obtaining a set of contig sequences comprising $T_0$ contig sequences, obtaining a set of paired end reads, wherein at least 1% of the paired end reads comprise a read pair distance of at least 1 kb, wherein the set of paired end reads comprises paired end reads in a natural orientation, wherein the sequencing error rate for the read pairs is no more than 0.1%, and outputting a scaffold comprising $T_1$, wherein $T_1 < T_0$. In some cases $T_1$ is less than 3. Optionally, the error rare is no greater than 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.001%, 0.0001%, or 0.00001% or less. Alternately, $T_1$ is selected to be less than 10, 9, 8, 7, 6, 5, or 4. In some cases $T_1$ is two, and in some cases $T_1$ is a single contig. $T_1$ is less than 50%, 40%, 30%, 20%, 10% 5%, 3%, 2%, 1%, or less than 1% of $T_1$ in many cases. The contig information is derived from a genome in many cases. Alternately, the contig sequence information is derived from a plurality of genomes. In some embodiments, the methods are practiced on a computer-implemented system comprising a processor configured to receive contig and read pair data as discussed herein, process the data as discussed above, and output scaffolded contig data having the improved parameters as discussed above.

Provided herein are methods of nucleic acid sequence data processing comprising: receiving an input data comprising read pairs, at least 1% of said read pairs comprising sequence data from two nucleic acid segments separated by at least 1 kb and in a natural orientation, wherein an RN50 for the input data is no greater than 20% of the assembled scaffold and wherein an error rate for said input data is no greater than 0.1%; and outputting an output data comprising a scaffold, wherein RN50 for the output data is at least 2× the RN50 of the input. In some methods RN50 for the output data is at least 10× the RN50 of the input, or alternately 3×, 4×, 5×, 6×, 7×, 8×, 9×, 11×, 12×, 13×, 14×, 15×, 16×, 17×, 18×, 19×, 20×, 30×, 40×, 50×, 60×, 70×, 80×, 90×, 100×, 500×, 1000×, or greater than 1000×. Further provided herein are methods wherein the scaffold comprises at least 90% of a target genomic sample sequence in correct order and orientation. Further provided herein are methods wherein the scaffold comprises at least 99% of a target genomic sample sequence in correct order and orientation. In some embodiments, the methods are practiced on a computer-implemented system comprising a processor configured to receive contig and read pair data as discussed herein, process the data as discussed above, and output scaffolded contig data having the improved parameters as discussed above.

Provided herein are methods of nucleic acid sequence data processing comprising: outputting a dataset comprising read pairs, at least 1% of said read pairs comprising sequence data from two nucleic acid segments separated by at least 1 kb and in a natural orientation, wherein an RN50 for the output data is no greater than 20% of the assembled scaffold and wherein an error rate for said output data is no greater than 0.1%; and receiving an dataset comprising a scaffold, wherein RN50 for the output data is at least 2× the RN50 of the input. In some methods the RN50 for the output data is at least 10× the RN50 of the input, or alternately 3×, 4×, 5×, 6×, 7×, 8×, 9×, 11×, 12×, 13×, 14×, 15×, 16×, 17×, 18×, 19×, 20×, 30×, 40×, 50×, 60×, 70×, 80×, 90×, 100×, 500×, 1000×, or greater than 1000×. Further provided herein are methods wherein the scaffold comprises at least 90% of a target genomic sample sequence in correct order and orientation. Further provided herein are methods wherein the scaffold comprises at least 99% of a target genomic sample sequence in correct order and orientation. In some embodiments, the methods are practiced on a computer-implemented system comprising a processor configured to receive contig and read pair data as discussed herein, process the data as discussed above, and output scaffolded contig data having the improved parameters as discussed above.

Provided herein are methods of nucleic acid sequence data processing comprising: receiving an input data comprising read pairs, at least 1% of said read pairs comprising sequence data from two nucleic acid segments separated by at least 1 kb and in a natural orientation, wherein an N50 for the input data is no greater than 20% of the assembled scaffold and wherein an error rate for said output data is no greater than 0.1%; and outputting an output data comprising a scaffold, wherein N50 for the output data is at least 2× the RN50 of the input. Optionally, the error rare is no greater than 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.001%, 0.0001%, or 0.00001% or less. The contig information is derived from a genome in many cases. Alternately, the contig sequence information is derived from a plurality of genomes. In some embodiments, the methods are practiced on a computer-implemented system comprising a processor configured to receive contig and read pair data as discussed herein, process the data as discussed above, and output scaffolded contig data having the improved parameters as discussed above.

Provided herein are methods of nucleic acid sequence data processing comprising: outputting an output data comprising read pairs, at least 1% of said read pairs comprising sequence data from two nucleic acid segments separated by at least 1 kb and in a natural orientation, wherein an N50 for the output data is no greater than 20% of the assembled scaffold and wherein an error rate for said output data is no greater than 0.1%; and receiving an input data comprising a scaffold, wherein N50 for the output data is no greater than 20% of the assembled scaffold. The contig information is derived from a genome in many cases. Optionally, the error rare is no greater than 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.001%, 0.0001%, or 0.00001% or less. Alternately, the contig sequence information is derived from a plurality of genomes. In some embodiments, the methods are practiced on a computer-implemented system comprising a processor configured to receive contig and read pair data as discussed herein, process the data as discussed above, and output scaffolded contig data having the improved parameters as discussed above.

Provided herein are methods of assessing the likelihood of joining two nucleic acid contigs sharing at least one paired end read, comprising: determining a density of mapped shotgun reads to the first contig, determining a density of mapped shotgun reads to the second contig, determining a likelihood score for joining the first contig and the second contig, and reducing the likelihood score when the density of mapped shotgun reads to the first contig differs significantly from the density of mapped shotgun reads to the second contig. In some methods the likelihood score is a log likelihood score. Often, the score is reduced as indicated herein. Often, the score is reduced as a ratio of the smaller to the larger of density of mapped shotgun reads to the first contig and the density of mapped shotgun reads to the second contig. The contig information is derived from a genome in many cases. Alternately, the contig sequence information is derived from a plurality of genomes. In some embodiments, the methods are practiced on a computer-implemented system comprising a processor configured to receive contig and read pair data as discussed herein, process the data as discussed above, and output scaffolded contig data having the improved parameters as discussed above.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims and in summary and detailed description herein. A better understanding of the features and advantages of the disclosure will be obtained by reference to the following detailed description that sets forth illustrative embodiments, in which the principles of the disclosure are utilized, and the accompanying drawings of which.

FIG. 4A depicts data for an 80 Kb inversion with flanking 20 kb repetitive regions. FIG. 4B depicts data for a phased heterozygous deletion.

DETAILED DESCRIPTION

Figure 1:
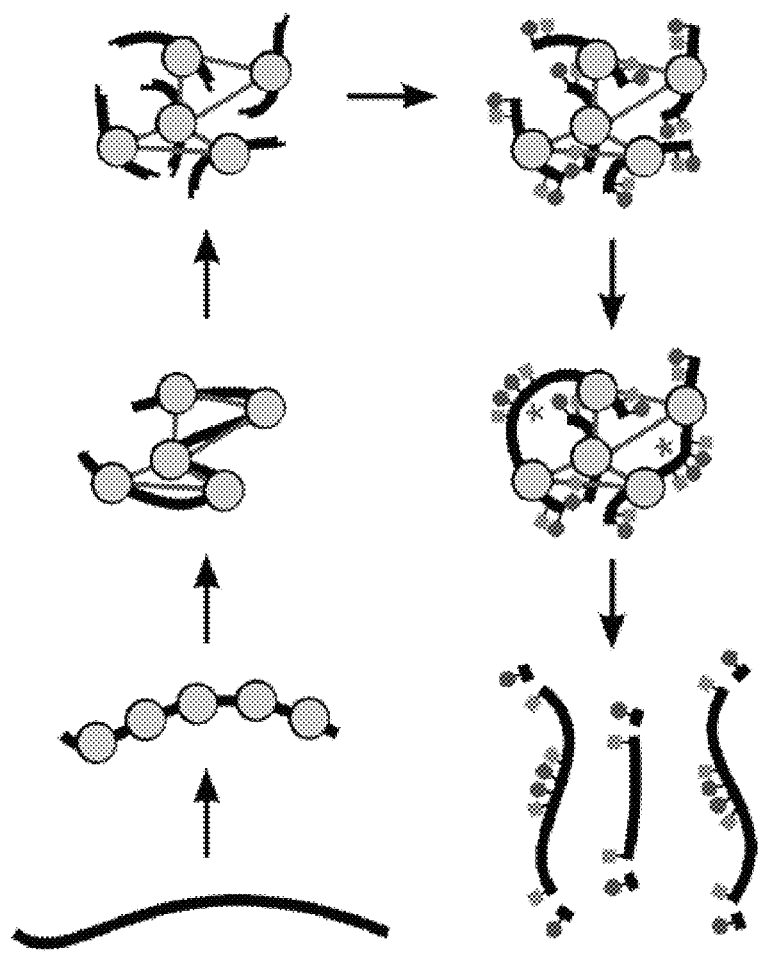
FIG. 1 depicts a flow process for generating material for de novo sequencing.

Long-range and highly accurate de novo assembly from short-read data is one of the most pressing challenges in genomics. We demonstrate here that DNA linkages up to several hundred kilobases can be produced in vitro using reconstituted chromatin rather than living chromosomes as the substrate for the production of proximity ligation libraries. The resulting libraries share many of the characteristics of Hi-C data that are useful for long-range genome assembly and phasing, including a regular relationship between within-read-pair distance and read count. Combining this in vitro long-range mate-pair library with standard whole genome shotgun and jumping libraries, we generated a de novo human genome assembly with long-range accuracy and contiguity comparable to more expensive methods, for a fraction of the cost and effort. This method only uses modest amounts of high molecular weight DNA, and is generally applicable to any species. Here we demonstrate the value of this sequence data not only for de novo nucleic acid sequence assembly (for example, into a scaffold representative of a genome or set of chromosomes) or scaffold assembly using human and alligator, but also as an efficient tool for the identification of structural variations and the phasing of heterozygous variants.

Disclosed herein are sequence assembly approaches based in exemplary embodiments on in vitro reconstituted chromatin. Through the methods, systems and compositions herein, a highly accurate de novo assembly and scaffolding of genomic or other large sequence data sets is accomplished, such that contigs grouped in phase, ordered, oriented, merged or spit as appropriate. Similarly, utility is demonstrated for improving existing assemblies by re-assembling and scaffolding contig and scaffold sequence information previously available. In some cases, with a single library and one lane of Illumina HiSeq sequencing to generate read pairs, a scaffold N50 is increased from about 500 kbp to 10 Mbp. Methods disclosed herein can be used to analyze any nucleic acid sample (e.g., a genome or plurality of genomes), and are particularly suitable for genome samples comprising hard to assemble, transposon- or other repeat element rich repetitive or polyploid genomes, or other samples that result in sample read data sets that are computationally intensive to assemble, particularly in no more than 8, 7, 6, 5, 4, 3, 2, or less than 2 hours.

As used herein and in the appended claims, the singular forms "a," "and," and "the" include plural referents unless the context clearly dictates otherwise. Thus, for example, reference to "a contig" includes a plurality of such contigs and reference to "probing the physical layout of chromosomes" includes reference to one or more methods for probing the physical layout of chromosomes and equivalents thereof known to those skilled in the art, and so forth, unless as indicated by context to refer to a single entity. Also, the use of "and" means "and/or" unless stated otherwise. Similarly, "comprise," "comprises," "comprising," "include," "includes," and "including" are interchangeable and not intended to be distinguishing.

It is to be further understood that where descriptions of various embodiments use the term "comprising," those skilled in the art would understand that in some specific instances, additional distinct embodiments are implied that are alternatively described using language "consisting essentially of" or "consisting of".

The term "read" or "sequencing read" as used herein, refers to sequence information of a segment of DNA for which the sequence has been determined.

The term "contigs" as used herein, refers to contiguous regions of DNA sequence. "Contigs" can be determined by any number methods known in the art, such as, by comparing sequencing reads for overlapping sequences, and/or by comparing sequencing reads against databases of known sequences in order to identify which sequencing reads have a high probability of being contiguous. Contigs are often assembled from individual sequence reads or previously assembled sequence information in combination with sequence reads having overlapping end or edge sequence. Generally but not exclusively, contigs comprise overlapping sequence reads that assemble into a larger sequence grouping, in many cases without intervening gaps or regions of undetermined sequence, or alternately without regions of known sequence and unknown length.

The term "scaffold" as used herein refers to sequence information from at least one contig or sequence read corresponding to a single physical molecule, such that all sequence information of a scaffold shares a common phase or reflects that the nucleic acids of which the sequence information is representative are physically linked. In some cases, scaffold sequence is not assembled into a single contig, but may have at least one gap between its constituent contigs or sequence reads, of unknown sequence, unknown length, or unknown sequence and unknown length. In some such cases, gapped sequences nonetheless constitute a single scaffold because of the fact that the constituent sequence is found to be in phase or to map to a single physical molecule. In some cases a scaffold comprises a single contig—that is, in some cases, a scaffold comprises a contiguous stretch of sequence without any gaps.

As a verb, the term to "scaffold" refers to at least one of ordering, orienting merging end to end, merging one within another, and breaking contigs or scaffolds, up to and including all of ordering, orienting merging end to end, merging one within another, and breaking contigs or scaffolds, such as is done informed by the methods presented herein. Scaffolding can be performed to assemble a plurality of contigs onto a single phase of a single molecule, onto a plurality of scaffolds, such as may arise from mapping contigs onto chromosomes of a eukaryotic organism, or may correspond to the genomes of a plurality of organisms in a heterogeneous sample.

As used herein, a "natural orientation" in the context of a paired read refers to a paired read wherein the paired sequences occur in an orientation representative or the orientation of the nucleic acid molecule segments from which they are derived.

The term "subject" as used herein can refer to any eukaryotic or prokaryotic (eubacterial or archaeal) organism or virus. A subject can alternately refer to a sample, independent of its organismal origin, such as an environmental sample comprising nucleic acid material from a plurality of organisms and/or viruses. For example, a subject can be a mammal, such as a human, or can be a sample taken from, say, a gut of a human, which is expected to comprise both human and substantial nonhuman nucleic acid sequence.

The terms "nucleic acid" or "polynucleotide" as used herein can refer to polymers of deoxyribonucleotides (DNA) or ribonucleotides (RNA), in either single- or double-stranded form. Unless specifically limited, the term encompasses nucleic acid molecules containing known analogues of naturally occurring nucleotides that have similar binding properties as the reference nucleotides and/or are metabolized in a manner similar to naturally occurring nucleotides.

The term "naked DNA" as used herein can refer to DNA that is substantially free of complexed proteins or nanoparticles.

The term "reconstituted chromatin" as used herein can refer to chromatin formed by complexing isolated nuclear proteins or other nucleic acid biding moieties to naked DNA. In some cases reconstituted chromatin in fact comprises nucleic acids and chromatin constituents, such as histones, while in alternate embodiments "reconstituted chromatin" is used more informally to refer to any complex formed from naked DNA or extracted DNA in combination with at least one nucleic acid binding moiety, such as a protein, nanoparticle or non-protein molecule such as spermidine or spermine, for example, that specifically or nonspecifically binds a nucleic acid.

The term "nanoparticles" as used herein can refer to nanometer-scale spheres that can be modified to bind DNA. In some cases nanoparticles are positively charged on their surfaces (e.g. by coating with amine-containing molecules). See Zinchenko, A. et al. (2005) "Compaction of Single-Chain DNA by Histone-Inspired Nanoparticles" *Physical Review Letters*, 95(22), 228101, which is herein incorporated by reference in its entirety. In some embodiments reconstituted chromatin is synthesized by binding nanoparticles to naked DNA.

The term "read pair" or "read-pair" as used herein can refer to two or more spans of nucleic acid sequence that are nonadjacent in a naturally nucleic acid molecule sample but are adjacently covalently linked as a result of chemical or enzymatic manipulations as disclosed herein or elsewhere, and are sequenced as a single sequencing read. In some cases "read pair" refers to the sequence information obtained by sequencing across two nucleic acid regions that are artificially joined. In some cases, the number of read-pairs can refer to the number of mappable read-pairs. In other cases, the number of read-pairs can refer to the total number of generated read-pairs.

As used herein, a 'sample' refers to nucleic acid material for which scaffold information is to be generated or improved. Some samples are derived from a homogenous source, such as a cell monoculture or a tissue from a single multicellular individual. In some cases a sample comprises sequence variation, such as variation that may arise in a tumor sample from an individual. In some cases a sample is derived from a heterogeneous source, such that it comprises nucleic acids from a plurality of organisms, such as a human gut or excrement sample, an environmental sample or a mixture of organisms.

As used herein, the term "about" a number is used to refer to the number quantity plus or minus 10% of that number, in addition to reciting that number explicitly.

Unless defined otherwise, all technical and scientific terms used herein have a meaning as commonly understood to one of ordinary skill in the art to which this disclosure belongs. Although methods and reagents similar or equivalent to those described herein can be used in the practice of the disclosed methods and compositions, the exemplary methods and materials are now described.

Disclosed herein are compositions, systems and methods related to sequence assembly, such as nucleic acid sequence assembly of single reads and contigs into larger contigs and scaffolds through the use of sequence grouping information such as read pair sequence information, such as read pair information indicative of nucleic acid sequence phase or physical linkage.

A major goal of genomics is the accurate reconstruction of full-length haplotype-resolved chromosome sequences with low effort and cost. Currently accessible and affordable high-throughput sequencing methods are best suited to the characterization of short-range sequence contiguity and genomic variation. Achieving long-range linkage and haplotype phasing requires either the ability to directly and accurately read long (e.g., tens of kilobases) sequences, or the capture of linkage and phase relationships through paired or grouped sequence reads. These methods are both technically challenging and computationally intensive, such that routine or commercial computational analysis of sequence information necessary to generate full-sample haplotype map information for a genomic sample is precluded.

High-throughput sequencing methods have sparked a revolution in the field of genomics. By generating data from millions of short fragments of DNA at once, the cost of re-sequencing genomes has fallen dramatically, rapidly approaching $1,000 per human genome (Sheridan, 2014), and is expected to fall still further.

Substantial obstacles remain, however, in transforming short read sequences into long, contiguous genomic assemblies. The challenge of creating reference-quality assemblies from low-cost sequence data is evident in the comparison of the quality of assemblies generated with today's technologies and the human reference assembly (Alkan et al., 2011).

Many techniques including BAC clone sequencing, physical maps, and Sanger sequencing, were used to create the high quality and highly contiguous human reference standard with a 38.5 Mbp N50 length and error rate of 1 per 100,000 bases (International Human Genome Sequencing Consortium, 2004). In contrast, a recent comparison of the performance of whole genome shotgun (WGS) assembly software pipelines, each run by their creators on very high coverage data sets from libraries with multiple insert sizes, produced assemblies with N50 scaffold length ranging up to 4.5 Mbp on a fish genome and 4.0 Mbp on a snake genome (Bradnam et al., 2013).

High coverage of sequence with short reads is rarely enough to attain a high-quality and highly contiguous assembly. This is due primarily to repetitive content on both large and small scales, including the repetitive structure near centromeres and telomeres, large paralogous gene families like zinc finger genes, and the distribution of interspersed nuclear elements such as LINEs and SINEs. Such difficult-to-assemble content composes large portions of many eukaryotic genomes, e.g. 60-70% of the human genome (de Koning et al., 2011). When such repeats cannot be spanned by the input sequence data, fragmented and incorrect assemblies result. In general, the starting point for de novo assembly combines deep coverage (50×-200× minimum), short-range (300-500 bp) paired-end "shotgun" data with intermediate range "mate-pair" libraries with insert sizes between 2 and 8 kbp, and often longer range (35 kbp) fosmid end pairs Gnerre et al., 2011; Salzberg et al., 2012).

Low-cost sequence data is useful, but is difficult to assemble into larger contigs or into scaffolds to which phase information can be ascribed. Accordingly, valuable information regarding genomic rearrangements, or even simpler information regarding the phase of multiple mutations dispersed within a single gene locus (cis or trans, corresponding to two independently mutated alleles or a single wild-type allele in combination with a doubly-mutant allele) is often not available from some low-cost sequence assemblies.

A number of methods for increasing the contiguity and accuracy of de novo assemblies have recently been developed. Broadly, they either attempt to increase the read lengths generated from sequencing or to increase the insert size between paired short reads. For example, the PacBio RS II can produce raw reads up to 23 kbp (median 2 kbp) in length. However, this approach has been reported to suffer from error rates as high as ~15% and remains ~100-fold more expensive than high-throughput short reads (Koren et al., 2012; Quail et al., 2012). Commercially-available long-reads from Oxford Nanopore are promising but often have even higher error rates and lower throughput. Illumina's TruSeq Synthetic Long-Read technology (formerly Moleculo) is currently limited to 10 kbp reads maximum (Voskoboynik et al., 2013).

Despite a number of improvements, fosmid library creation (Williams et al., 2012; Wu et al., 2012) remains time-consuming and expensive.

To date, the sequencing community has not settled on a consistently superior technology for large inserts or long reads that is available at the scale and cost needed for large-scale projects like the sequencing of thousands of vertebrate species (Haussler et al., 2009) or hundreds of thousands of humans (Torjesen, 2013).

Disclosed herein are methods for nucleic acid sequence assembly. Methods disclosed herein are particularly suited for analysis and sequence improvement using paired-end reads. Paired end reads or read pairs are generated using a number of different approaches. Some approaches involve in vitro methods for producing long-range read pairs, separated by up to hundreds of kilobases, and their use in assigning common phase or physical linkage information to the contigs to which each read in a read pair maps. Central to some embodiments of the disclosure herein is an unexpectedly effective improvement of Hi-C that takes advantage of the relationship between distance and read count to produce long-range read pair data useful for improving de novo scaffold assembly and phasing. Unlike its predecessor Hi-C methods, some approaches disclosed herein use in vitro reconstituted chromatin as a substrate for fixation, paired end formation, and subsequent steps. The resulting data share many of the characteristics of Hi-C data, including the relationship between read pair count and distance between reads. However, in many embodiments the paired end reads generated thereby lack information regarding three-dimensional chromatin or other nucleic acid configuration within the host cell, information that is a particularly valuable objective of Hi-C technology, but which may involve proximity information of nucleic acid sequence from molecules that are not in phase or physically linked to one another. These new in vitro data can be used in isolation or can be combined with paired-end shotgun reads or other previously generated contig information to generate de novo scaffold assemblies with accuracy and contiguity comparable to fosmid-based assemblies for a fraction of the price and time. The methods, compositions and systems related to analysis of such advances are disclosed herein, as is their utility for improving the quality of de novo assemblies, phasing haplotypes and identifying structural variants.

The disclosure herein provides methods and computational systems that can produce a highly contiguous and accurate human genomic assembly using no more than about 10,000, about 20,000, about 50,000, about 100,000, about 200,000, about 500,000, about 1 million, about 2 million, about 5 million, about 10 million, about 20 million, about 30 million, about 40 million, about 50 million, about 60 million, about 70 million, about 80 million, about 90 million, about 100 million, about 200 million, about 300 million, about 400 million, about 500 million, about 600 million, about 700 million, about 800 million, about 900 million, about 1 billion read pairs, or greater than 1 billion base pairs. In some cases, the disclosure provides methods and computational systems that phase about 50%, 60%, 70%, 75%, 80%, 85%, 90%, 91%, 92%, 93%, 94%, 95%, 96%, 97%, 98%, 99% or more of heterozygous variants in a human genome with about 50%, 60%, 70%, 75%, 80%, 85%, 90%, 91%, 92%, 93%, 94%, 95%, 96%, 97%, 98%, 99%, or greater accuracy.

Compositions and methods related to read-pair end generation and sequencing and alternate methods of generating tagged end reads are found, for example, in US Publication No. US20140220587, published Aug. 7, 2014, which is hereby incorporated by reference in its entirety.

Embodiments disclosed herein comprise at least one of the following steps, up to and including each of the following steps, alone or in combination with additional steps disclosed herein or known to one of skill in the art:
1. Input pre-processing
2. Contig-contig linking graph construction
3. Seed scaffold construction
4. Local order, orientation, and gap size refinement
5. Computation of scores for pairwise scaffold merging
6. Greedy acceptance of joins In some embodiments, a series of the above-mentioned steps are performed in combination. In some cases at least one of steps 4, 5, and 6 is performed iteratively, for example to effect an ongoing improvement of the assembly quality.

Some methods and systems disclosed herein contemplate three inputs:
1. The sequence of a starting assembly (optionally in FASTA format);
2. Alignments of paired reads to the starting assembly (optionally in BAM format, sorted and indexed);
3. Alignments of shotgun reads to the starting assembly (optionally in BAM format, sorted and indexed).

Alternative data formats are contemplated and the methods and systems are not limited to a specific data format or indexing. The starting assembly comprises at least one contig assembled from sequence reads, and in some cases comprises at least one scaffold comprising at least one contig, independent of sequence format.

Paired reads, paired end reads, or read pairs as alternately referred to comprise sequence information corresponding to nonadjacent, target sample sequence, independent of sequence format. In many cases the paired reads correspond to read sequences of a single physical molecule, from positions separated by long distances of the common molecule in a sample nucleic acid sequence.

Disclosed herein are methods and computational systems for assembling contig data into scaffolds representing at least one of their relative position, relative orientation, of the contigs relative to one another. In some cases individual contigs are merged in the process, either by joining adjacent contigs whose position and/or orientation is determined, or by inserting at least one contig into a gap or unassembled region of a second scaffold or contig, to form a contig or scaffold of comparable size but improved sequence quality.

Paired-end read information for a sample is generated using methods disclosed herein, incorporated herein or otherwise known to one of skill in the art. In some cases tagged end reads, such as paired tagged end reads, are substituted for paired end reads as discussed elsewhere herein. In some instances the paired end read or other information is used in combination with contig information such as shotgun sequencing contig information, in some cases concurrently generated and in other cases independently obtained, for example from a previous sequencing effort or shotgun sequencing effort performed in parallel. In some cases the contig information is obtained from a sequence database or a previous sequencing effort.

Paired end reads are generated as disclosed herein, or through other methods known to one of skill in the art or compatible with the disclosure herein. Minor and major variations in paired read generation are contemplated. Paired reads comprise a pair of read sequences that are not adjacent in the sample material prior to processing. In most cases, the paired reads map to a single physical molecule, but some distance from one another. In some cases paired reads are generated comprising pairs from distinct physical molecules. In the methods disclosed herein, such paired end reads are relatively rare, and they are often excluded from analysis early in the assembly processes disclosed herein.

Among paired end reads where both reads arise from a single physical molecule, some paired reads arise from regions that are no more than 100, 200, 300, 400, 500 or more than 500 base pairs apart, while some paired reads arise from sequence that is separated by 1, 2, 3, 4, 5, 6, 7, 8, 9, 10, 15, 20, 25, 30, 35, 40, 45, 50, 60, 70, 80, 90, 100 kb, or more than 100 kb on a single physical molecule. Often, a set of paired end reads includes a distribution of paired end read distances, such that some read pairs represent nucleic acid segments in their natural orientations.

In some embodiments, the methods disclosed herein group contigs in a manner independent of the number of chromosomes for the organism. A more conservative threshold on contig-contig links for single-link clustering is applied than in some related techniques to assemble the resulting smaller contig clusters into scaffolds, with subsequent scaffolding joining possible by various methods disclosed herein. A benefit in these embodiments is that an assembly error is not 'propagated' by compensatory errors to force an expected total chromosome length or number. Using methods dependent upon chromosome size or number, one misplaced contig often leads to multiple errors, as the correct contig or scaffold displaced by the misplaced contig assembled or scaffolded at its position must be 'forced' into a second position so as to preserve overall chromosome number or length at the expense of sequence accuracy.

Paired end sequences are mapped to contig information and, in some cases, previously existing scaffold information such as the sequence information available for the complete human genome project. Paired ends are selected in some cases such that one or both sequences of a pair uniquely map to a single contig or unique region of a scaffold. For paired end reads where both reads of the pair uniquely map to a distinct position that can be determined relative to one another on a contig or scaffold, the distance between reads in a pair is determined. Read-pair distance frequency curves are calculated from this data, and in some cases extrapolated to provide frequency estimates for a given read pair distance across a broad range of read pair distances. Consequently, for a single read pair for which two or more than two distinct read pair distances are possible, for example corresponding to two or more than two relative orientations of one contig to a second contig, one can determine which contig orientation corresponds to the more likely read pair distance. Similarly, when a plurality of read pairs map to a pair of contigs, one can determine the most likely read pair distance for each read pair individually and for the aggregate distance for the set. In some cases, one determines the 'aggregate most likely orientation' of a given contig pair by evaluating the relative impact of contig orientation on a plurality of read pair distances, and selecting the orientation that leads to the set of read pair distances that is, in aggregate, more or most likely.

Generally, for an individual read pair, and for most read pair distance distributions, the shorter read pair distance is the more likely. However, when a plurality of read pair distances are evaluated for a single pair of contigs or a plurality of contigs, the most likely read pair distribution comprises in some cases both short and long read pair distances, such that the distribution of read pair distances most closely reflect the predicted read pair distributions, rather than a simple minimization of aggregate read pair length.

Figure 2:
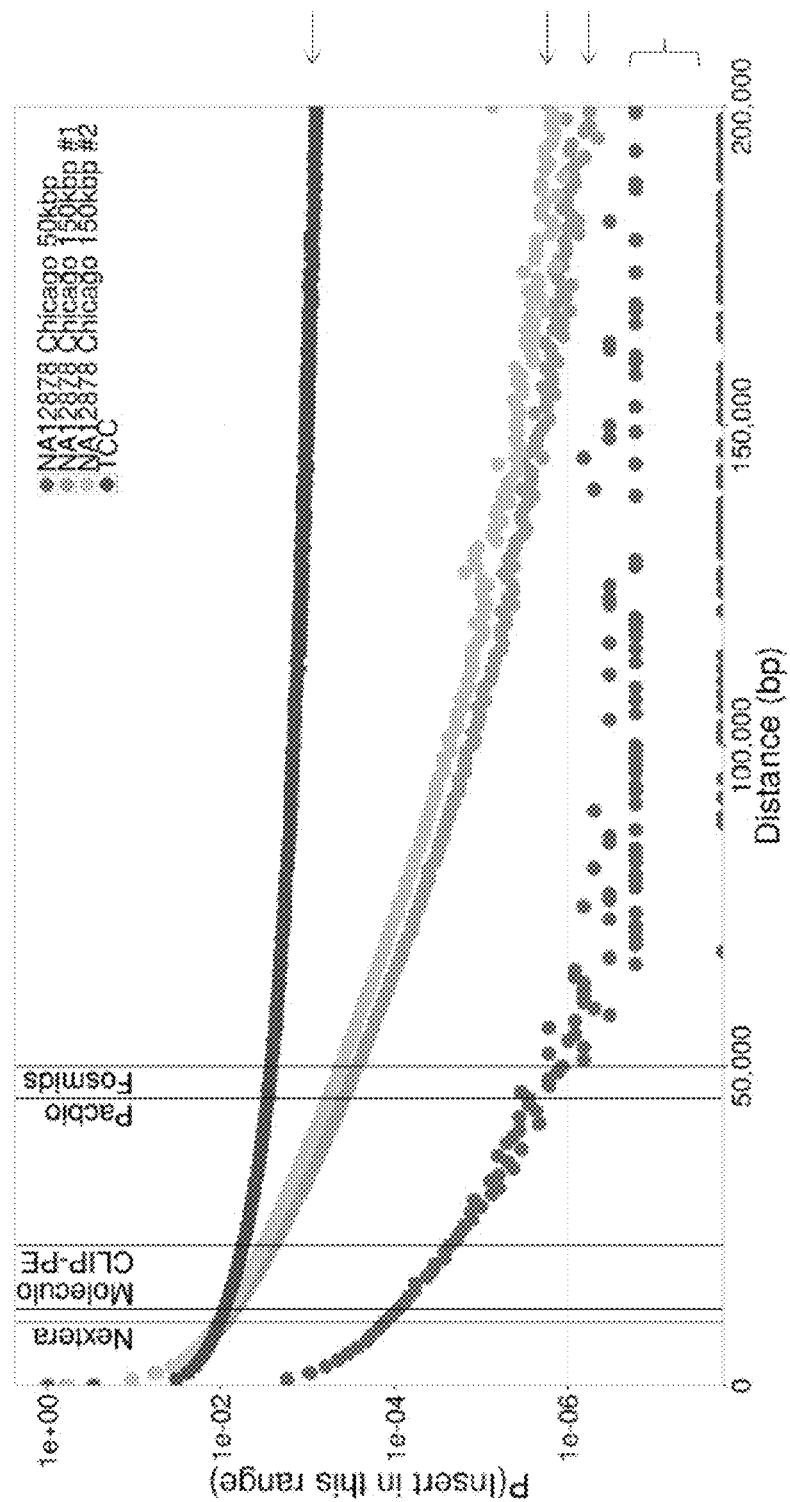
FIG. 2 illustrates read pair separations for several sequencing libraries mapped to the reference human genome assembly hg19.

In FIG. 2, one sees example read-pair distance frequency curves as described herein. Data are presented as frequency of occurrence as a function of read-pair distance, and are observed to decrease 'exponentially' or 'logarithmically' with increasing read pair distance. Alternate data depictions are consistent with the disclosure herein.

In some cases, read-pair distance curves are independently determined when a set of read-pair data is generated for a sample. Alternately or in combination, previously determined read pair data are used to generate a read pair distance curve. In some cases a previously generated or independently generated read pair curve or curves are used.

To assemble contigs into scaffolds having order information or orientation information or order and orientation information, paired-reads are selected where both reads of the pair uniquely map to a distinct position, but for which the distinct position of the two reads of the read pair cannot be determined relative to one another on a contig or scaffold. This situation occurs, for example, when distinct reads of a read pair map to separate contigs that are not positioned with confidence on a common scaffold, or if separate data otherwise casts doubt on the position of one contig relative to another, such that the distance, orientation or distance and orientation of the contigs relative to one another is not known.

Optionally, read pair sequences are culled prior to contig analysis, such that poor quality reads are excluded. In some cases read pair sequences are culled prior to contig analysis, such that read pairs having at least one read that does not uniquely map to a single contig are excluded. In some cases read pair sequences are culled prior to contig analysis, such that read pairs having at least one read that does not uniquely map to a single position per contig to which it maps are excluded. In some cases read pairs are culled if at least one of their sequence pair maps to a region to which a disproportionate number of read pair sequences maps, for example as identified by a spike in read pair 'hits' across a depiction of a pre-scaffolded sequence data set or a data set that has been subjected to a sequence assembly. In some culling approaches, a step size is defined, e.g. 1000 bp, and at each step, the support for joined contigs is calculated with and without the bins of read pairs flanking the joined region, which may make up most of the support for the join. Alternate step sizes, such as 100, 200, 300, 400, 500, 600, 700, 800, 900, 1,500, 2,000, 3,000, 4,000, 5,000, 10,000 or greater than 10,000 are also contemplated. If a bin has a number of read pairs above a threshold based on the mean, median or average hit distribution, it is excluded. In some cases the threshold is selected to be 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.5×, 5×, or greater than 5× of a mean, median or average value. Parameters and criteria for sequence read culling are known to one of skill in the art, and a number of culling parameters are contemplated herein. In some cases, any read that overlaps by at least a single base with a bin to which the greatest number of reads map is excluded from analysis.

Contigs are grouped relative to one another to generate initial contig positionings. A number of approaches for contig positioning are contemplated herein, and alternative embodiments differ in their choice of initial contig order and/or orientation. For example, in some cases, contigs are mapped onto a previously generated draft or complete genome scaffold or chromosome map. Such a map is obtained from a previous sequencing of a target species, from a previous sequencing of a closely related species such as a related species for which significant genome-scale synteny is expected or known, or for a separate population of the species from which a representative's genome is being sequenced. For example, a Neanderthal genome is mapped against a human genome scaffold, a wild Solenaceae family member is mapped against a cultivated tomato (*Lycopersicon esculentum*) genome, or a particular plant cultivar is arranged according to the nearest sequenced genome of a close relative. Other methods of initial contig positioning, such as ordering using an alternate method or computational system of phase determination known in the art, are contemplated and consistent with the disclosure herein.

In some cases contigs are grouped according to the number of shared read pairs. That is, in some cases, contigs sharing a greater number of read pairs are grouped closely to one another, while contigs that share few read pairs are positioned relatively far apart from one another.

For some local groupings, the contigs are linearly arranged. However, initial groupings often present considerable branching or cyclic contig orientations, and in some cases initial groupings comprise substantially larger groups than are predicted based upon, for example known genetic information about genetic or physical linkage groups, or known cytological information regarding chromosome numbers.

In some cases an initial grouping is evaluated as to the strength of the relationships among contigs as represented by their shared paired end reads. Contigs having less than a threshold value of paired end reads are separated in some cases, for example if the number of shared paired end reads is not more than 2, 3, 4, 5, 6, 7, 8, 9, 10, 11, 12, 13, 14, 15, or a threshold number greater than 15 in some cases.

Contigs sharing at least one read pair are identified and grouped into a single physical linkage group. In some cases contigs are grouped into a single physical linkage group if they share at least 2, 3, 4, 5, 6, 7, 8, 9, 10, 11, 12, 13, 14, 15, 16, 17, 18, 19, 20 or more than 20 paired-end reads. In some cases this threshold value varies according to the nucleic acid sample being sequenced.

In some cases contigs are preliminarily ordered relative to one another, based for example upon previously generated or previously obtained scaffold information, or the total number of read pairs shared across contigs, or the total number of read pairs shared across contigs normalized by contig length or unique contig sequence.

As an alternative to counting the raw number of shared read pairs, in some cases contigs are evaluated as to the read-pair distances for each read pair, and read pairs having distances for which a probability value falls below a threshold are excluded from the assessment of common read pairs.

Thus the determination that a pair of contigs warrant proximal grouping in an initial assessment (that is, whether they are provisionally assigned to a common 'edge') is determined by either the aggregate number of shared paired reads or by the number of shared paired reads having a threshold distance probability. In some cases alternate assessments of paired end read relevance to contig edge determination are used.

Contigs are positioned into locally linear arrangements. In some cases locally linear arrangements are bordered by breakpoints having insufficient read pairs to link them to another contig at one end. In some cases locally linear arrangements are bounded at one end by a branch point, whereby a single contig is bound equally stringently at one end to two separate contigs. In some cases linear arrangements of contigs bounded at one end by a branch point are broken at the branch point, and treated as separate linear groupings. Alternately, in some cases, branch point junctions are broken and reassembled under alternate assembly conditions, such that under the altered or second set of assembly conditions the branches are no longer equally likely, and a single branch is selected to continue the linear arrangement of contigs.

In some cases, particularly for short branches or branches involving short contigs, a branch represents a contig or linear series of contigs that maps between the other edge contigs in the branch point. Small contigs are, by chance or otherwise, less likely to be the map destination of a large number of read pair ends. As a result, short contigs may only have one or a few read pair ends mapping to them, resulting in a predicted linkage to only one adjacent contig. This situation is often observed when one member of a branch point is a singleton contig or a linear grouping or cluster of contigs that collectively do not represent a relatively long sequence. In some cases, small branch point contigs or linear sequences of contigs are assessed for the impact upon the read-pair distances and read pair distance probabilities for various assemblies of the adjacent linear contig series, such that small branch point contigs or linear sequences of contigs are inserted at branch points if the local impact on read pair distances is favorable. In some cases, the impact of contig or contig series insertion on read pair distance is assessed by comparing the relative impact on read pair edge scores of the inserted contig or contig series as inserted relative to the same contig or series of contigs being inserted at a position that is far removed from the insert site.

Figure 10:
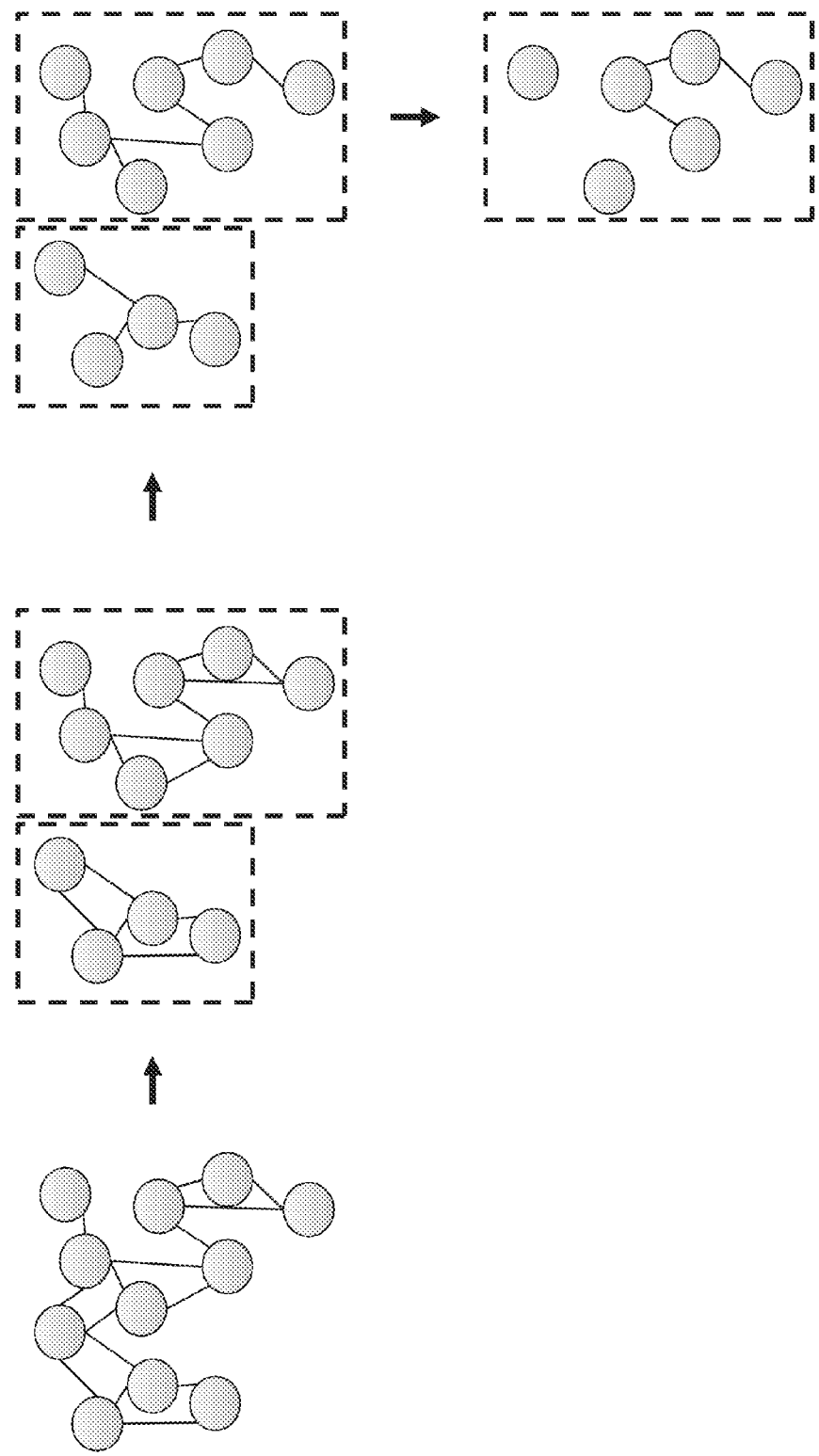
FIG. 10 depicts an exemplary workflow from initial contig assembly through generation of linear ordered contigs for 'window' analysis.

A schematic depiction of initial contig linear grouping is presented in FIG. 10. Contigs are depicted as circles, and contig pair edges are depicted as lines. At the upper left of FIG. 10, viewed landscape, one sees an initial grouping. The initial grouping is relatively low stringency in some cases, and all contigs are linked into a single cluster. At the upper center of FIG. 10, contig edges are evaluated and low-stringency linkages between contigs, scaffolds or nodes are removed. The subsequent high-stringency groupings often correspond to or map to linkage groups (chromosomes or chromosome sections). At the upper right of FIG. 10, cycles within the graphs are removed by breaking the weaker or less probable remaining edges to form branched trees. At the lower right of FIG. 10, branched trees are broken at branch points to yield linear scaffolds. In some cases, recursive window analysis is performed on the linear scaffolds depicted in the lower right of FIG. 10.

Figure 11:
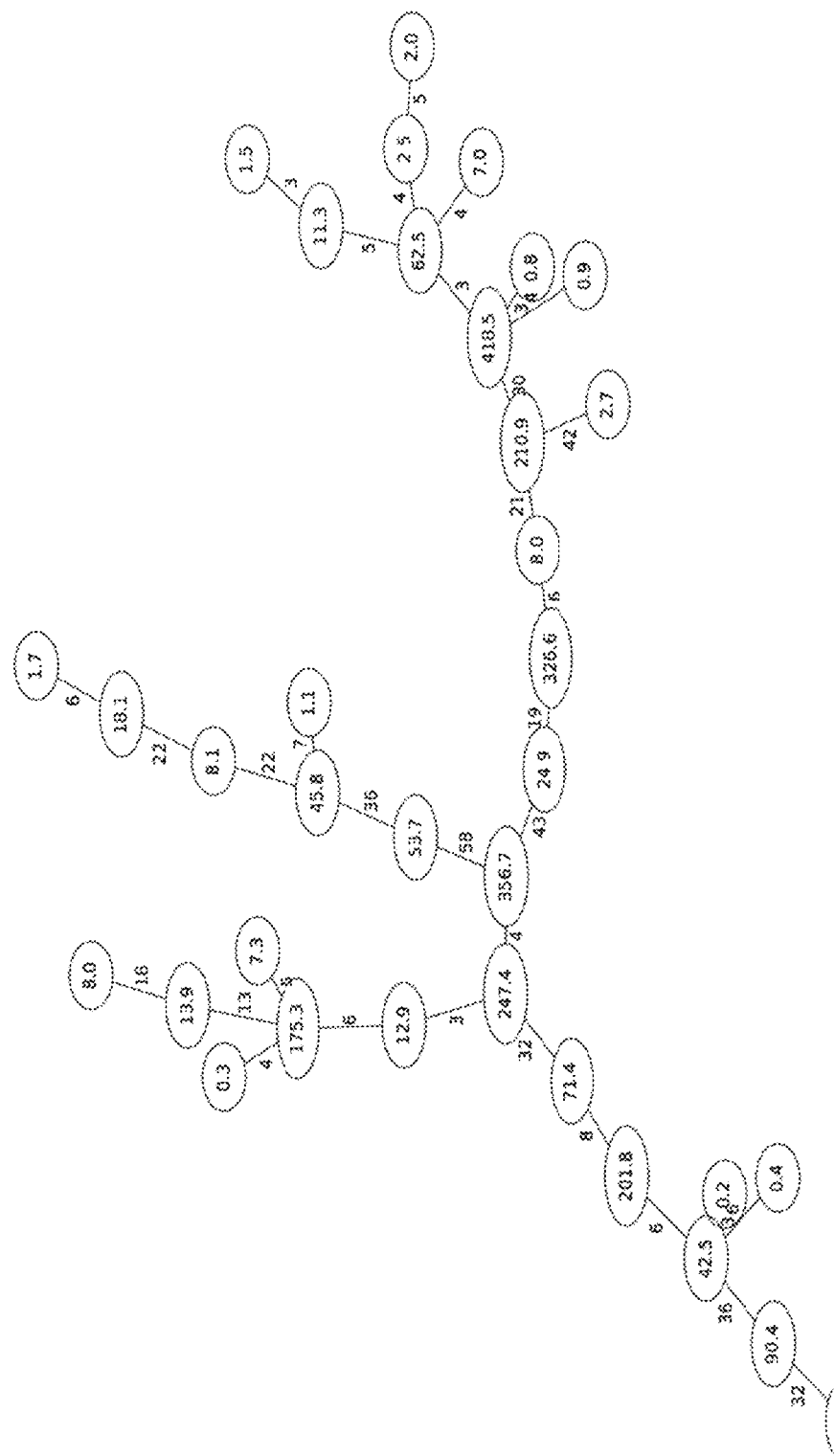
FIG. 11 depicts a minimum spanning tree. Node labels indicate contig size in kb, and edge labels indicate the number of links at each indicated contig pair edge.

FIG. 11 depicts an exemplary minimum spanning tree. Cycles have been broken, but multiple branches are depicted in the cluster. Contigs are indicated as nodes, with length indicated within each oval, and the number at each contig pair edge indicates the number of read pairs supporting that edge. One observes that the majority of branches at this stage correspond to short groupings of small contigs or contig groups. Often, these branches are found on further analysis to map between adjacent nodes or to map to a gap or region of undetermined sequence within a node, such as the node to which they are mapped as adjacent to. One reason that small scaffolds, contigs or nodes often appear as branches is that, because their lengths are relatively short, they are less likely to be hit by read pair sequences mapping to each adjacent node.

Upon grouping the contigs into locally linear order, using a method as disclosed herein or an alternate method of ordering, contigs are repositioned using a locally exhaustive assessment of read pair distance probabilities.

A linear grouping of contigs is identified and a 'window' or locally adjacent subgroup of contigs is selected, such as a subgroup at one end of a linear group of contigs. Alternately, contigs that are grouped into local clusters or groupings divisible into a target 'window size' are analyzed below, even if their grouping is not linear. A number of window sizes are compatible with the disclosure herein, from a window size of 2, 3, 4, 5, 6, 7, 8, 9, 10, or more than 10, up to and including the full length of a linear grouping of contigs. In some exemplary embodiments the window size is 3 or 4. Generally, greater window sizes provides greater computational confidence that the ultimate order is at an optimum with regard to an evaluated contig read pair characteristic or metric (such as maximum likelihood of the predicted read pair distances, minimum overall deviation from the expected likelihood distances, minimum overall distance, or alternate metric). However, greater window sizes require substantially greater computational time, and in some cases or on some computer systems, larger window sizes are computationally prohibitive as to time or cost. Window sizes of 3-4 are found to achieve a scaffolding accuracy that approximates that of larger windows without the additional computational time necessary to exhaustively explore the added window sizes.

Often, a single window size is selected to accommodate a desired computational burden or computational time, and is used iteratively on an entire scaffold or contig data set. However, alternatives are also consistent with the methods disclosed herein. Window sizes will in some cases vary according to different regions of a dataset, such that windows are defined so as to include a minimum or maximum or average target number of mapped read pairs common to the window. Alternately or in combination, window sizes are in some cases selected to reflect the computational complexity of the underlying sequence, such that computationally challenging regions such as repetitive regions or sequences of poor sequence quality are provided with greater or less computational power relative to regions of more straightforward sequence. In some cases window size is informed by a minimum or maximum spanned contig sequence length, alone or in combination with a factor recited elsewhere herein. For well-characterized genomes, window size is optionally altered to accommodate transposon-rich regions, telomeres, centromeres, ribosomal repeat regions, and/or complex or repetitive loci.

For each read pair, or for a subset of the read pairs, of a set of contigs within a window, each of four orientations for the two contigs to which the pair maps relative to one another are assessed as to the distance impact that a given orientation has upon the distance between at least one read pair up to and including each read pair shared between the two contigs. In some cases the probability of distance combinations are determined such that, for a given orientation, one can assess the aggregate relative probability of that orientation relative to the other orientations of the contigs. In some methods disclosed herein, the orientation yielding the highest aggregate distance probability is selected as the most likely reflection of the physical position of the contig sequences relative to one another. In some cases the orientation yielding read pair distances that represent the lowest deviation from the expected read pair distributions is selected. Other ordering criteria are contemplated in alternate embodiments, such as minimizing total read pair length, or minimizing the number of read pairs above a threshold length, or alternate criteria.

As discussed elsewhere herein, in some embodiments groups of more than two contigs are assessed as to their order, orientation or order and orientation. In some cases, a 'window' of 2, 3, 4, 5, 6, 7, 8, 9, 10, or more than 10 contigs are assessed simultaneously to determine their orientation, order, or orientation and order relative to one another. As a practical matter, computational time discourages analysis of groupings greater than about 4 contigs in a given window. However, analysis of larger numbers of contigs at once in a single window is contemplated, as are variants as discussed above and elsewhere herein.

Looking at the window analysis in more detail, methods and computational systems disclosed herein for refining configuration of contigs given a probabilistic model of the separations of read pairs linking them were developed and tested. Some methods relate to a dynamic programming algorithm that slides a window of size w across an initial ordering of a cluster of contigs. At a plurality of positions i up to in some cases each position i, it considers all the w! $2^w$ ways of ordering and orienting the contigs within the window, and stores a score representing the optimal ordering and orientation of all the contigs up to the end of the current window position that ends with the current configuration of the contigs in the window. To do so it looks at the scores of "compatible" orders and orientations in windows at positions i-1, i-2 . . . i-w, and scores the extension of their orderings with the current configuration. Since w! $2^w$ is such a steep function, the method is limited to small values of w in practice. In tests on some data, w=3 is capable of dramatically improving configuration accuracy for some datasets. Alternate window sizes are contemplated, as are alternate rationales for constant and variable window size selection. Upon finding an optimal or locally maximal score for a window, contigs are scaffolded so achieve said optimal or locally maximal score. The window is then advanced one position and the analysis is repeated.

Window analysis differs from some embodiments of the initial contig ordering process because, unlike an initial ordering, the window analysis is often locally exhaustive of all possible contig configurations, including both contig orders and contig orientations, and the impact of each configuration on read pair lengths and on read pair length probabilities relative to a calculated or previously determined read pair length probability curve. That is, in some window analyses, all possible contig configurations within the window are assessed, and in some cases all possible impacts of contig configuration on read pair length are determined and assessed as to which read pair length combination, reflected in the contig or scaffold ordering and orienting, is locally most probable in light of a read pair length probability curve.

A number of methods and algorithms are available for computation of the relative aggregate probabilities for a set of read pairs shared between two contigs. One exemplary algorithm disclosed herein is as follows:

$$L(l1, l2, g, o,) = \frac{N!}{(N-n)!}(1-p_o)^{N-n}\prod_{i=1}^{n} f(d_i). \quad \text{(Formula 1)}$$

This likelihood function gives the probability of observing the number n and implied separations of spanning read pairs $d_i$ between contigs 1 and 2, assuming the contigs have relative orientations o, o∈++, +−, −+,−− and are separated by a gap of length g.

It is understood that alternative algorithms are contemplated and are consistent with the disclosure herein. Some algorithms involve assessing the total read pair distance for relative contig orientations, such that a minimum total read pair distance is assessed and an orientation corresponding to a minimum total read pair length is selected. Alternatively or in combination, variation of read pair distances for a given contig orientation set from an expected read pair distribution pattern is assessed, and a contig orientation that minimizes such variation is selected.

As discussed above, in some embodiments a window of 2, 3, 4, 5, 6, or more than 6 contigs is assessed as to the scaffolding such as relative order, orientation or configuration of its constituent contigs. Upon determining a scaffold comprising an order, orientation or configuration for a set of 2, 3, 4, 5, 6, or more than 6 contigs that minimizes or reduces or minimizes in light of external constraints the aggregate relative distance frequencies for read pairs common to two of the contigs in the group, or an order that maximizes the likelihood of occurrence of the predicted read pair distances, the contigs in that group are ordered and oriented accordingly.

Upon ordering, orienting, or ordering and orienting a set of contigs in a given window, one terminal contig in the order as optimally determined is excluded, and the remaining contigs are analyzed again in combination with one additional new contig, again identified as putatively representing an adjacent contig, based upon a preliminary ordering of the contigs, as discussed herein.

This process is repeated, for example unidirectionally from one end of a putative contig order, through to the other end. In alternative embodiments, window orienting begins at a random position within an ordered contig set and proceeds unidirectionally toward a contig edge, or stepwise bidirectionally toward both edges, or begins at either end of a scaffold and proceeds through to an internal meeting point.

In alternate embodiments windows are 'moved' by two or three contigs at a step such that two or three adjacent contigs are removed from one side of an ordered window of contigs and a corresponding number are added at the other side, rather than through exclusion of a single contig and addition of a single contig at a time.

Window analysis is continued in some cases until a majority, up to all contigs of a group, are ordered so as to minimize or maximize a parameter as selected herein. A common feature of many embodiments of the window analysis is that, for the contigs in a given window, all orientations are exhaustively analyzed, such that a local maximum or minimum yielding orientation is exhaustively searched for, and in some cases a local maximum or minimum parameter related to read pair distance, is identified for a subset of window contig groups up to and including each contig in a grouping of contigs.

The contig orientation resulting from a partially complete or complete window analysis represents in some cases a contig orientation that is identical to or substantially similar to a globally optimized contig orientation, such as would be generated by exhaustively analyzing all contigs in a single scaffold or data-set sized 'window'. However, by using the window analysis herein, substantially less contig orientation space need be analyzed to come to a locally optimized contig orientation, and substantially less computer time or calculation capacity need be occupied to come to the locally optimal orientation.

In some embodiments, (i) a model of insert distributions is constructed based on observed data distributions of read pairs from a known sequence library, (ii) read pairs generated are individually ranked against the model; (iii) based on comparison to the model, a read pair is given a score, and (iv) read pairs with high scores are those that most closely fit the model.

In some embodiments, (i) a model of insert distributions is constructed based on observed data distributions of read pairs from a previously unmapped sequence library, (ii) the read pairs generated are then individually ranked against the model; (iii) based on comparison to the model, a read pair is given a score, (iv) read pairs with high scores are those that most closely fit the model, and (v) the model is altered in order to generate scores that create a more likely arrangement of contigs within a scaffold.

In some cases, a recursive algorithm is used in which one window (w) views 1, 2, 3, 4, or more contigs at a time and only overlapping windows are viewed at any one time. Due to the recursive nature of the algorithm, the windows gradually march through contigs on a scaffold or other grouped nucleic acid dataset until the windows march to an endpoint or return to a starting place in the scaffold.

Paired end reads generated through a number of protocols are consistent with the analysis herein. In some embodiments, a DNA extraction protocol is used, including methods of DNA extraction that are known in the art. In some embodiments, a commercially available DNA extraction kit is used. Exemplary commercially available DNA extraction kits include Qiagen Blood and Cell Midi kits. In some embodiments, the starting tissue for DNA extractions is a bodily fluid or tissue from a human. In some embodiments the sample for DNA extraction is from a non-human animal, a plant or a fungus. In some embodiments, the source of DNA is from a microorganism or virus.

In some embodiments, cell nuclei are isolated from cells using a cell lysis and centrifugation protocol or any other method of cell isolation that is known in the art. In some embodiments, nuclei are digested with enzymes to degrade non-DNA cellular components. Exemplary enzymes include Proteinase K and RNAse A. In some embodiments, cellular or viral DNA is purified and isolated using methods well known in the art. An exemplary kit is a Qiagen genomic column in which the DNA is be washed, eluted and precipitated in isopropanol and pelleted by centrifugation. After drying, the pellet is resuspended in 200 µL TE (Qiagen). In alternate embodiments, nucleic acids are isolated from whole cells or from samples comprising multiple cell types or nucleic acids from multiple sources. In some embodiments, DNA is synthesized de novo.

In some cases, paired ends are generated though the re-ligation of cleaved clusters of reassembled chromatin, so as to preserve physical linkage information during double strand cleavage. Chromatin is re-assembled with purified DNA using any methods known in the art. For example, chromatin is assembled overnight at 27° C. from genomic DNA using the Active Motif in vitro Chromatin Assembly kit. In further embodiments, a test is done following incubation to confirm successful chromatin assembly. An example test is the use of 10% of the sample is for MNase digestion to confirm successful chromatin assembly. 'Reassembled chromatin' is used very broadly, to refer both to reconstitution of biological chromatin constituents such as histones or nucleosomes or other nuclear proteins such as transcription factors, DNA binding proteins, transposases, or other nuclear proteins involved with nucleic acid binding, and to artificial reconstituted chromatin, as is generated by addition of non-protein nanoparticles onto a nucleic acid molecule.

Chromatin is labeled in some cases with a reagent that facilitates binding chromatin to sorting reagents or isolation of bound pairs. In one example, the labeling reagent is biotin. In a more specific example, chromatin is biotinylated with iodoacetyl-PEG-2-biotin (IPB). In some embodiments, a complex of DNA and chromatin is subject to fixation with a fixation reagent. In some cases, the DNA-chromatin complex is fixed in 1% formaldehyde at room temperature (RT) for 15 minutes, followed by a quench with 2-fold molar excess of 2.5M Glycine. In some embodiments, a DNA-chromatin complex is subject to a reaction that creates DNA fragments. In some embodiments, a DNA-chromatin complex is subject to digestion with a restriction enzyme. In some cases, the DNA is digested with either MboI or MluCI.

Un-bound streptavidin sites are optionally occupied by incubating beads in the presence of free biotin for 15 minutes at RT. In some embodiments, sticky ends are filled in by incubating with dNTPs, e.g., a-S-dGTP and biotinylated dCTP. In some embodiments, a ligation step is conducted to join the blunt ends generated by dNTP fill-in. In some embodiments, DNA is digested with an exonuclease to remove biotinylated free ends. In some cases, the exonuclease is exonuclease III (#M0206S, NEB).

In some embodiments, DNA is subjected to shearing. In further embodiments, sheared DNA is filled in with Klenow polymerase and T4 PNK. In some embodiments, following the fill-in reaction, DNA is enriched, e.g., by a pulled down reaction.

In some embodiments, sequence reads are defined by junctions generated by the restriction enzyme digestion recognitions cites selections. For example, where MboI and MluCI are used, sequence reads are truncated whenever a junction was present (GATCGATC for MboI, AATTAATT for MluCI). In some embodiments, reads are then aligned using SMALT [which can be accessed at the website indicated by sanger.ac.uk/resources/software/smalt/] with the -x option to independently align forward and reverse reads. In some embodiments, PCR duplicates are marked using Picard-tools MarkDuplicates [which can be accessed at the website indicated by broadinstitute.github.io/picard/]. In some embodiments, non-duplicate read pairs are used in analysis where both reads mapped and had a mapping quality greater than 10.

Scaffolding—Input Pre-processing

Input preprocessing is optionally employed prior to or independent of window analysis. Paired reads that map to highly repetitive regions of an assembly or contig set or scaffold set are removed from further analysis, so as to clean the read pair population so that it includes uniquely mapping sequence. In some cases, the alignment of whole genome shotgun reads to the assembly is used to identify these regions. Alternately or in addition, read pairs mapping to an interval of the starting assembly having a mapped shotgun read depth exceeding a threshold are excluded. It is observed that some regions are 'hot spots' for read pairs, and that inclusion of pair data from such hotspot regions may bias downstream analysis. In some cases a two-threshold method is used, such that if an interval contains at least one base with a mapped read depth exceeding a 'trigger' t2, then all reads mapping to that interval with a depth exceeding a 'cutoff' t1 are excluded. In some cases, a double threshold strategy is used such that: all intervals of the starting assembly with mapped shotgun read depth exceeding t1 that contain at least one base with a mapped read depth exceeding t1 or t2 are identified and excluded. In some exemplary embodiments, t1 and t2 are selected such that about 0.5% of the assembly is masked, or such that 0.05, 0.1, 0.2, 0.3, 0.4, 0.5, 0.6, 0.7, 0.8, 0.9, 1.0, 1.1, 1.2, 1.3, 1.4, 1.5, 2, 3, 4, 5, 6, 7, 8, 9, 10, 15, 20, 30, 40, 50, 60, 70, 80, or more that 80% of an assembly is masked. In some embodiments, t1 and t2 are set such that about 0.5% of the assembly was masked. In some cases the percent of the assembly to be masked is influenced by the proportion of the assembly that is repetitive. In some embodiments, a set the thresholds on the depth of mapped shotgun reads is t1 is 3× and t2 is 3.5×, where x equals the mean of the overall distribution of depths. For example, in the case of a particular human assembly, t1 is 87, t2 is 102, such that if a threshold of 102 is reached, then regions having hits to a depth of 87 or greater are masked. In this example, 'x' is 29, 3× is 87 and 102 is 3.5×. In some embodiments t1 is selected from less than 2×, 2.0×, 2.1×, 2.2×, 2.3×, 2.4×, 2.5×, 2.6×, 2.7×, 2.8×, 2.9×, 3.0×, 3.1×, 3.2×, 3.3×, 3.4×, 3.5×, 3.6×, 3.7×, 3.8×, 3.9×, 4.0× or greater than 4.0×. In some embodiments t2 is selected from less than 2×, 2.0×, 2.1×, 2.2×, 2.3×, 2.4×, 2.5×, 2.6×, 2.7×, 2.8×, 2.9×, 3.0×, 3.1×, 3.2×, 3.3×, 3.4×, 3.5×, 3.6×, 3.7×, 3.8×, 3.9×, 4.0×, 4.1×, 4.2×, 4.3×, 4.4×, 4.5×, 4.6×, 4.7×, 4.8×, 4.9×, 5.0×, or greater than 5.0×.

In some cases read pairs are excluded if they fall within a 1 Kbp window on the assembly which is linked to more than four other input contigs by at least two read pair links. In some cases the exclusion window is less than 100 bp, 100 bp, 200 pb, 300 pb, 400 pb, 500 pb, 600 pb, 700 pb, 800 pb, 900 pb, 1 kb, 1.1 kb, 1.2 kb, 1.3 kb. 1.4 kb. 1.5 kb, 2 kb, 3 kb, 4 kb 5 kb or greater than 5 kb. In some cases the exclusion window is triggered if the region is linked to 2, 3, 4, 5, 6, 7, or more than 7 other input contigs.

Scaffolding—Estimation of Likelihood Model Parameters

In some cases likelihood model parameters are estimated prior to input processing. Several steps of the methods and systems disclosed herein can use a likelihood model of the read pair data to guide assembly decisions or to optimize contig configuration within scaffolds. In some embodiments, a likelihood is used to guide assembly decisions or to optimize contig configuration within scaffolds. In some cases, the likelihood function is:

$$L(l1, l2, g, o,) = \frac{N!}{(N-n)!}(1-p_o)^{N-n}\prod_{i=1}^{n} f(d_i) \quad \text{(Formula 1)}$$

This likelihood function gives the probability of observing the number n and implied separations of spanning read pairs $d_i$ between contigs 1 and 2, assuming the contigs have relative orientations o, o∈++, +−, −+,−− and are separated by a gap of length g. The function $f(x)$ is the normalized probability distribution over genomics separation distances of read pairs, and is assumed to have a contribution from "noise" pairs which sample the nucleic acid sample independently. $f(x)=p_n/G+(1-p_n)f'(x)$, and $f'(x)$ (Formula 2) is represented as a sum of exponential distributions. Alternative functions comprising the assessment of at least one of these parameters are contemplated as consistent with the disclosure herein.

In some embodiments, to obtain robust estimates of N, $p_n$, G, and $f'(x)$ when the available starting assembly has limited contiguity, an estimate of the product $N p_n$, the total number of "noise" pairs by tabulating the densities of links (defined as $n/l_1 l_2$) for a sample of contig pairs, excluding the highest and lowest 1% of densities, and setting $N_n=G^2\Sigma n_{ij}/\Sigma l_i l_j$ (Formula 3), using the sum of the lengths of input contigs as the value of G. In some cases, the remaining parameters are fixed in N $f(x)$ by least squares to a histogram of observed separations of read pairs mapped to starting assembly contigs, after applying a multiplicative correction factor of $G(\Sigma_{i=1}^{N_c} \min(0, l_i-x))^{-1}$ (Formula 4) to the smoothed counts at separation x. Alternative equations and mathematical representations of the concepts herein are contemplated as consistent with some embodiments of the methods and systems herein.

Scaffolding—Metagenomic Likelihood Model Parameters

In some exemplary embodiments, input data is obtained from a sample comprising a mixture of nucleic acids from multiple sources (e.g., metagenomic library). In some such situations, a likelihood model used in several methods and computational systems disclosed herein is modified to account for input data derived from mixed nucleic acid samples or metagenomic libraries. In some cases, it is assumed that likelihood scores are being computed for two fragments with respective lengths (e.g., $l_1$ and $l_2$) and counts (e.g., $s_1$ and $s_2$). In some cases, the counts can be any quantity which is approximately proportional to the product of a fragment's length and its relative abundance in the input mixed nucleic acid sample. As a non-limiting example, $s_1$ and $s_2$ could be the number of reads mapping to each contig from an appropriate sequencing library. In some embodiments, the likelihood score is modified to account for the expected number of noise reads and read pairs. In some cases the likelihood score, $$S = \sum_i \ln \frac{f(x_i)}{f(\infty)} - (\bar{n} - \bar{n}_0), \quad \text{(Formula 5)}$$

is modified for the expected number of noise read $$\bar{n}_0 = Np\frac{l_1 l_2}{G^2} \rightarrow Np\frac{s_1 s_2}{S_T^2} \quad \text{(Formula 6)}$$

and read pairs $$\bar{n} = N\frac{1}{G}\int_A f(x)\,dxdy. \quad \text{(Formula 7)}$$

In some cases an effective total number of read pairs is calculated. In some cases, the effective total number of read pairs is $$N \rightarrow N\left(\frac{s_1 + s_2}{l_1 + l_2}\right)\left(\frac{G}{S_T}\right). \quad \text{(Formula 8)}$$

In some cases, a score penalty is applied, such as a score penalty that decreases the likelihood score as the discrepancy between the density of read pairs mapped to the two fragments to be joined increases. As a non-limiting example, a penalty is calculated as follows $$\Delta \ln \frac{L(H_1)}{L(H_0)} = \frac{Binom\left(s_1 \mid s_1 + s_2, \frac{l_1}{l_1 + l_2}\right)}{Poisson(s_1 \mid \lambda = s_1) Poisson(s_2 \mid \lambda = s_2)}. \quad \text{(Formula 9)}$$

Scaffolding—Break Low-support Joins in the Input Contigs

Input assembly data is optionally processed so that contigs, scaffolds or assembly information is partially disassembled, for example such that relatively weak assembly decisions are not perpetuated in downstream analysis. For example, to identify and break candidate misjoins in the starting assembly, the likelihood model is used to compute the log likelihood change gained by joining the left and right sides of each position i of each contig in the starting assembly (e.g., the log likelihood ratio (LLR) $L_i = \ln L(g=0) = L(g=\infty)$ for the two contigs that would be created by breaking at position i). In some embodiments, when this support falls below a threshold value $t_b$ over a maximal internal segment of an input contig, the segment is defined as a "low support" segment. In some embodiments, after merging low support segments lying within, for example, 300 bp of one another, and excluding those within, for example, 1 Kbp of a contig end, additional modifications are done depending on segment size. For example, a break is introduced in the contig at the midpoint of the segment for segments under 1000 bp or if the segment is longer than 1000 bp, then breaks are introduced at each end of the segment. In some cases breaks are introduced at each end of the segment if longer than 100 bp, 100 bp, 200 pb, 300 pb, 400 pb, 500 pb, 600 pb, 700 pb, 800 pb, 900 pb, 1 kb, 1.1 kb, 1.2 kb, 1.3 kb. 1.4 kb. 1.5 kb, 2 kb, 3 kb, 4 kb 5 kb or greater than 5 kb.

Scaffolding—Contig-contig Linking Graph Construction

During the assembly process, the generated linking data is optionally represented as a graph in which (broken) contigs of the starting assembly are nodes and edges are labeled with a list of ordered pairs of integers, each representing the positions in the two contigs of the reads from a mapped pair. In some embodiments, the initial steps of scaffolding is carried out in parallel on subsets of the data created by partitioning the graph into connected components by excluding edges with fewer than a threshold number of generated links $t_L$, where the lowest integer threshold that did not give rise to any connected components that comprised more than 5% of the input contigs. Depending on details of a particular data set or analysis system, the threshold $t_L$ is selected to exclude less than or about less than 0.5, 0.6, 0.7, 0.8, 0.9, 1.0, 1.1, 1.2, 1.3, 1.4, 1.5, 2, 3, 4, 5, 6, 7, 8, 9, 10, 15, 20, or greater than 20% of the input contigs.

Scaffolding—Seed Scaffold Construction

In some embodiments, the iterative phase of scaffold construction is seeded by filtering the edges of the contig-contig graph and decomposing it into high-confidence linear subgraphs. In some cases, the contig-contig edges are filtered and the minimum spanning forest of the filtered graph is found (see "edge filtering" below). In some cases, the graph is linearized by three successive rounds of removing nodes of degree 1 followed by removal of nodes with degree greater than 2. In some cases, each of the connected components of the resulting graph has a linear topology and defined an ordering of a subset of the input contigs. In some cases, a culminating step in the creation of the initial scaffolds is to find the maximum likelihood choice of the contig orientations for each linear component. In some embodiments the graph is linearized by 1, 2, 4, 5, 6, or more than 6 successive rounds of node removal. In some embodiments the degree of the node removed varies. In some cases the maximum likelihood choice is calculated using specific equations to determine maximum likelihood. In some cases the maximum likelihood is a general assessment of the most likely order, orientation or order and orientation.

Scaffolding—Edge Filtering

Filters are optionally applied to the edges of the contig-contig graph before linearization. Exemplary filters include the following: exclusion of edges with fewer than $t_L$ links and exclusion of edges from "promiscuous" contigs. "Promiscuous" contigs are identified as those for which the ratio of the degree in the graph of the corresponding node to the contig length in basepairs exceeds $t_p$, or have links passing filter (1) to more than $d_m$ other contigs. The thresholds $t_p$ and $d_m$ are selected in some cases to exclude approximately 5% of the upper tail of the distribution of the corresponding value. In some cases, the thresholds $t_p$ and $d_m$ were selected to exclude about less than 0.5, 0.6, 0.7, 0.8, 0.9, 1.0, 1.1, 1.2, 1.3, 1.4, 1.5, 2, 3, 4, 5, 6, 7, 8, 9, 10, 15, 20, or greater than 20% of the upper tail of the distribution of the corresponding value. In some embodiments, $t_L$, ranges from below 7, 7, 8, 9, 10, 11, 12, 13, 14, to 15 or more than 15. In some embodiments $t_p$ ranges from 0.01, 0.02, 0.03, 0.04, 0.05, 0.06, 0.07, 0.08, 0.09, to 0.1. In some embodiments $d_m$ ranges from less than 5, 5, 6, 7, 8, 9, 10, 11, 12, 13, 14, 15, or more than 15. In some embodiments it is found that an improved performance is obtained when, $t_L$, $t_p$, and $d_m$ are 11, 0.04, and 10, respectively.

Scaffolding—Contig Orienting

Each input scaffold has one of two orientations in a final assembly, corresponding to the base sequences of the forward and reverse, or "Watson" and "Crick" DNA strands. As disclosed herein, the optimal orientations for the scaffolds in each linear string is found by analysis such as dynamic programming using the recursion relationship as indicted below. In an ordered list of scaffolds of length n, the score of the highest scoring sequence of orientation choices for the scaffolds up to scaffold i, such that scaffolds i-k to i have particular orientations $o_{i-k}, o_{i-k+1}, \ldots o_i$ is given by:

$$S_m(i, o_{i-k}, o_{i-k+1}, \ldots, o_i) = \max_{o_{i-1-k} \in [+,-]} \left( S_m(i-1, o_{i-1-k}, o_{i-k}, \ldots, o_{i-1}) + \sum_{j=i-1-k}^{j=i-1} \log p(o_j, o_i) \right)$$

(Formula 10)

Optionally, including links from contigs k steps back provides an improvement in orientation accuracy. In some cases, the improvements in orientation accuracy arise because small intercalated scaffolds might only have linking and therefor orientation information on one side, with important orientation information for the flanking scaffolds coming from links that jump over it, in a situation similar to that resulting in branched contig ordering, as discussed above.

Scaffolding—Merge Scaffolds within Components

Contig ends are optionally designated classifications relative to their location in scaffold. For example, contig ends are classified as "free" if they lie at the end of a scaffold, or "buried" if they were internal to a scaffold. In some embodiments, for all pairs of contig ends within each connected component, the LLR score for joining them is computed with a "standard" gap size of $g_0$. In some embodiments, candidate joins are sorted in decreasing order of score and evaluated according to a set of criteria. An exemplary set of criteria follows. If both ends are free and from different scaffolds, test linking the two scaffolds end-to-end. If one end is buried and the other is free, and the ends are from different scaffolds, test inserting the scaffold of the free end into the gap adjacent into the buried end. If one or both ends is buried and the ends are on the same scaffold, test inverting the portion of the scaffold between the two ends. If both ends are buried and from different scaffolds, test all four ways of joining the scaffolds end-to-end. In some embodiments, for all cases, the possible joins, insertions and inversions are tested by computing the total change in LLR score by summing the LLR scores between all pairs of contigs affected by the change. If the change increased the LLR score, the best move is accepted.

Scaffolding—Local Order, Orientation and Gap Size Refinement

To refine both the local ordering and orientations of contigs in each scaffold, a dynamic programming algorithm is optionally applied that slides a window of size w across the ordered and oriented contigs of each scaffold. At each position i, all the $w!2^w$ ways of ordering and orienting the contigs within the window were considered, and a score representing the optimal ordering and orientation of all the contigs up to the end of the current window position that ends with the current configuration of the contigs in the window was stored. The scores of all "compatible" orders and orientations in windows at positions i-1, i-2, ... i-w, and scores the extension of their orderings with the current configuration were used. Since $w!2^w$ is such a steep function, the method is generally limited in practice to small values of w. In some embodiments, w is 2, 3, 4, 5, 6, 7, 8, 9, 10 or more. In tests on some exemplary data, w=3 dramatically improves configuration accuracy for some datasets. In some embodiments, a method for refining configuration of contigs given a probabilistic model of the separations of read pairs linking is provided. Such method is a dynamic programming algorithm that slides a window of size w across an initial ordering of the contigs.

Scaffolding—Iterative Joining

After the initial scaffolds had been constructed within each connected component, the resulting scaffolds are returned to a single pool, and multiple rounds of end-to-end and intercalating scaffold joins are carried out. In each round, all pairs of scaffolds are compared, and likelihood scores are computed in parallel for end-to-end and intercalating joins. The candidate joins are then sorted and non-conflicting joins are accepted in decreasing order of likelihood score increase.

Partitioning Advantages

Described here are methods for in vitro generation of long range mate-pair data that can dramatically improve the scaffolding of de novo assembled contigs from high-throughput sequencing data. These approaches have several advantages over existing methods.

First, data library construction does not require living biological material, e.g., primary or transformed tissue culture or living organism. Libraries described herein are generated from as little as 5.0 micrograms of input DNA or less, such as 10, 9, 8, 7, 6, 5, 4, 3, 2, 1 or less than 1 microgram. Furthermore, although the in vitro chromatin reconstitution is based on human histones and chromatin assembly factors, DNA from a wide variety of plants, animals, and microbes can be substrate for in vitro chromatin assembly using the protocol described.

Second, because data are generated from proximity ligation of chromatin assembled in vitro rather than chromatin obtained in vivo sources, there is no confounding biological signal to potentially confuse the assembly. Hi-C and or other proximity ligation data generated from in vivo chromatin carries within it long-range proximity information that is of biological relevance, but is persistent and potentially confounding for genome or scaffold assembly. In some embodiments, the methods provided here result in a low background rate of noise and a virtual absence of persistent and spurious read pairs.

Third, in contrast to in vivo Hi-C methods, the maximum separation of the read pairs generated is limited only by the molecular weight of the input DNA. This has allowed the generation of highly contiguous scaffolding of vertebrate nucleic acid scaffolds or genomes using just short fragment Illumina sequence plus the generated libraries.

Fourth, these libraries eliminate the need for creating and sequencing a combination of long range "mate-pair" and fosmid libraries, and do not require the use of expensive, specialized equipment for shearing or size-selecting high molecular weight DNA normally required to create such libraries.

Accordingly, DNA library construction methods and computational systems are provided which uses bioinformatics methods to generate significantly longer-range contig assembly scaffolds than existing methods. In some embodiments, the DNA library construction methods provided herein also provide for identifying nucleic acid sample or genome variation. Often, the DNA library construction methods and computational systems provided herein generate accurate reconstruction of full-length haplotype-resolved chromosome sequences with low effort and cost.

To improve both ordering and orientation accuracy, the ordering and orientation problems are solved by integrating the ordering and orientation steps. In one example, an initial graph was constructed such that in this graph, nodes are contig ends, and the two end-nodes of each contig are joined by an edge. The log-likelihood ratio scores of the inter-contig edges under an assumption of a specific short gap size, was computed and followed by sorting. Working down the list in decreasing order of edge score, new edges are either accepted or rejected according to whether they would increase or decrease the total score of the assembly. It is noted that even edges with a positive score could decrease the sum of scores of contigs in the assembly because accepting an edge which implies intercalation of a contig or contigs into the gap of an existing scaffold will increase the gap sizes between pairs of linked contigs on either side of the gap, which will potentially give them a lower score.

In addition, one improves the efficiency of computation of maximum likelihood gap sizes. Overall accuracy of the reported assembly is increased by estimating the length of unknown sequences between consecutive contigs. Given a model of the library creation process that includes a model probability density function (PDF) for the separation d between library read pairs, the maximum likelihood gap length can be found by maximizing the joint likelihoods of the separations $d_i$ of the pairs spanning the gap. For differentiable model PDF, the efficient iterative optimization methods (e.g. Newton-Raphson) is used.

Parameters for Identifying Success

A number of methods and computational systems herein involve the evaluation of at least two orders, orientations, scaffold connection states, contig breakage assessments, or other possible sequence repositionings (collectively, 'scaffolding'). A number of approaches are available to numerically assess a scaffolding that represents an improvement over starting or previous data. In exemplary embodiments, a contig or scaffold configuration is preferred if produces a read pair separation distance distribution curve that more closely approximates an expected, independently determined or concurrently determined curve (for example, from read pairs having ends that both map to the same contig). A curve more closely approximates an expected, independently determined or concurrently determined curve if, for example, it scores favorably in an evaluation using Formula 1, above. Alternate evaluations are available to one of skill in the art, such as analysis of variation (ANOVA) tests, assessments of covariation, or other tests.

Alternately or in combination, separate scores or metrics for global scaffolding effectiveness are used. Some measures involve percent alignment to a known nucleic acid assembly, such that a scaffolding that leads to an improvement in percent alignment is favored. In some cases the improvement leads to a percent alignment of at least 50%, 60%, 70%, 75%, 80%, 85%, 90%, 95%, 99%, 99.5%, 99.9%, or greater than 99.9%.

A second measure is the effect of scaffolding on an overall scaffold population, such as N50. That is, in some cases a scaffolding is preferred if the resultant N50 for the sequence dataset increases. In some cases the improvement leads to a percent increase of at least 0.5%, 1%, 2%, 3%, 4%, 5%, 10%, 20%, 30%, 40%, 50%, 60%, 70%, 80%, 90%, 100%, 150%, 200%, 250%, 300%, 400%, 500%, 600%, 700%, 800%, 900%, 1000%, 1500%, 2000%, 2500%, 3000%, 4000%, 5000%, 6000%, 7000%, 8000%, 9000%, 10,000%, 15,000%, 20,000%, 25,000%, 30,000%, 35,000%, 40,000%, 45,000%, 50,000%, 55,000%, 60,000%, 65,000%, 70,000%, 75,000%, 80,000%, 85,000%, 90,000%, 95,000%, 100,000%, or greater than 100,000%.

Alternately or in combination, additional metrics of effect on an overall scaffold population are used. One such metric is the RN50 measurement. An RN50 is understood as follows. For a set of sequences S and a reference sequence R, the RN50 or "referenced N50" of S with respect to R is the length of the shortest sequence in T, where T is the smallest (least cardinality) subset of S such that the sequences in T can be aligned to R in such a way that they cover at least 50% of the length of R.

Since all the sequences in T are at least as big as RN50, this means that a randomly selected base of R has at least a 50% probability of being spanned by an alignment to a sequence in T (and therefor in S) that is at least of length RN50.

In some cases an initial RN50 has a value that is 0.5%, 1%, 2%, 3%, 4%, 5%, 10%, 20%, 30%, 40%, or 50%, or another number within this range, of a sample sequence such as a genome sequence. In some cases the final RN50 has a value that is greater than the initial RN50. In some cases the improvement leads to a percent increase in RN50 of at least 0.5%, 1%, 2%, 3%, 4%, 5%, 10%, 20%, 30%, 40%, 50%, 60%, 70%, 80%, 90%, or greater than 90%, 100%, 2×, 5×, 10×, 20×, 50×, 100×, 200×, 500×, 1000×, 2000×, 5000×, 10000× or greater than 10000×.

Alternate metrics of scaffolding success consistent with the disclosure herein are contemplated.

Referring to the figures, FIG. 1 illustrates an exemplary schematic diagram of a DNA library generation protocol. At the upper left of FIG. 1, chromatin (nucleosomes depicted as circles) is reconstituted in vitro upon naked DNA (black strand). At the upper right center of FIG. 1, viewed landscape, chromatin is fixed with formaldehyde (thin lines are crosslinks). Fixed chromatin is pulled down onto streptavidin beads and cut with a restriction enzyme, generating free sticky ends, as shown in the upper right of FIG. 1. At the lower right of FIG. 1, sticky ends are filled in with biotinylated (smaller circles) and thiolated (small squares) nucleotides. At the lower center of FIG. 1, free blunt ends are ligated (ligations indicated by asterisks). At the lower left of FIG. 1, crosslinks are reversed and proteins removed to yield library fragments. Library fragments are digested to remove biotinylated nucleotides from unligated ends. Library fragments are selected with streptavidin coated beads, then have adapters ligated on in preparation for sequencing.

In some embodiments, comparing read pair separations for several generated libraries mapped to a reference assembly is used. For example, FIG. 2 provides an example of read pair separations for several generated libraries mapped to a reference human assembly, such as hg19. In the figure, the data trend marked by the lower bracket on the right of the plot corresponds to 50 Kbp input human sequencing library. The data trend marked by the lower arrow on the right of the plot corresponds to 150 Kbp input human sequence library. The data trend marked by the middle arrow on the right of the plot corresponds to 150 Kbp input human sequence library. The data trend marked by the top arrow on the right of the plot corresponds to a human Hi-C library (Kalhor et al., 2012). Dark vertical lines indicate maximum advertised or demonstrated capabilities for alternative mate-pair technologies.

Figure 3:
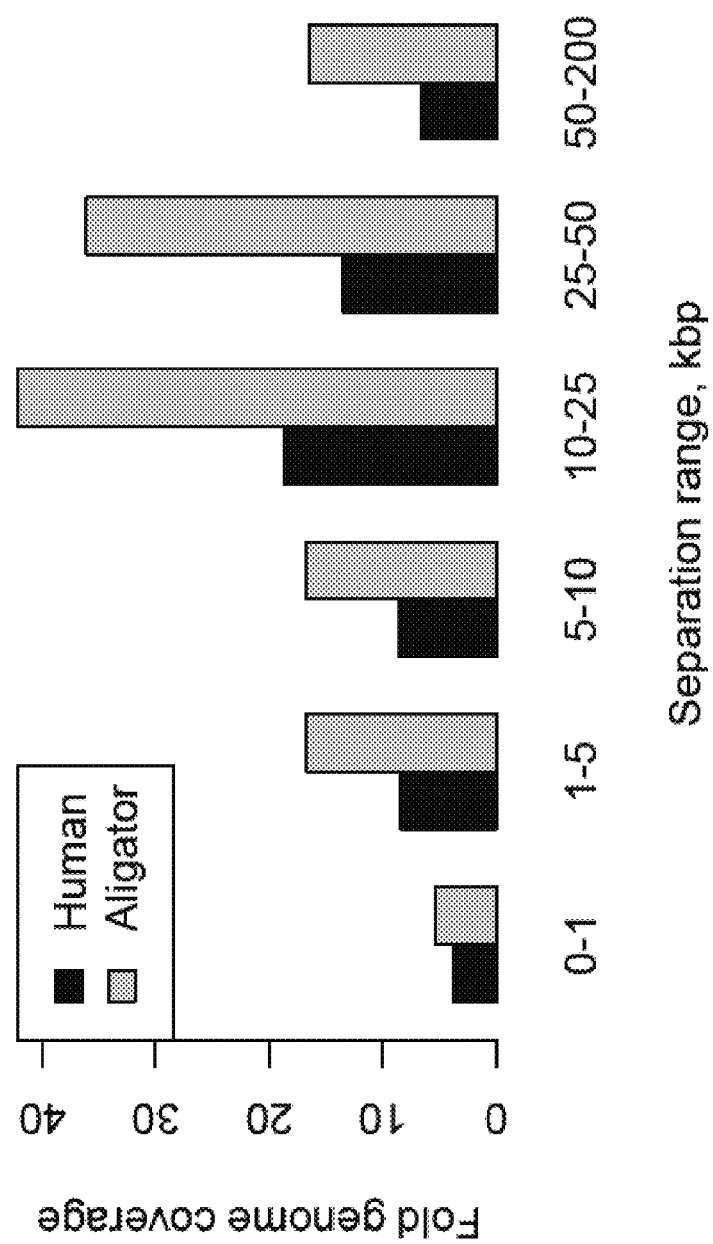
FIG. 3 is a chart of coverage (sum of read pair separations divided by estimated genome size) in various read pair separation bins.

The sum of read pair separations divided by estimate contiguous nucleic acid or genome size is calculated for various read pairs grouped by separation range as an alternative or additional metric. An exemplary summary of such a comparison is shown in FIG. 3.

Figure 4A:
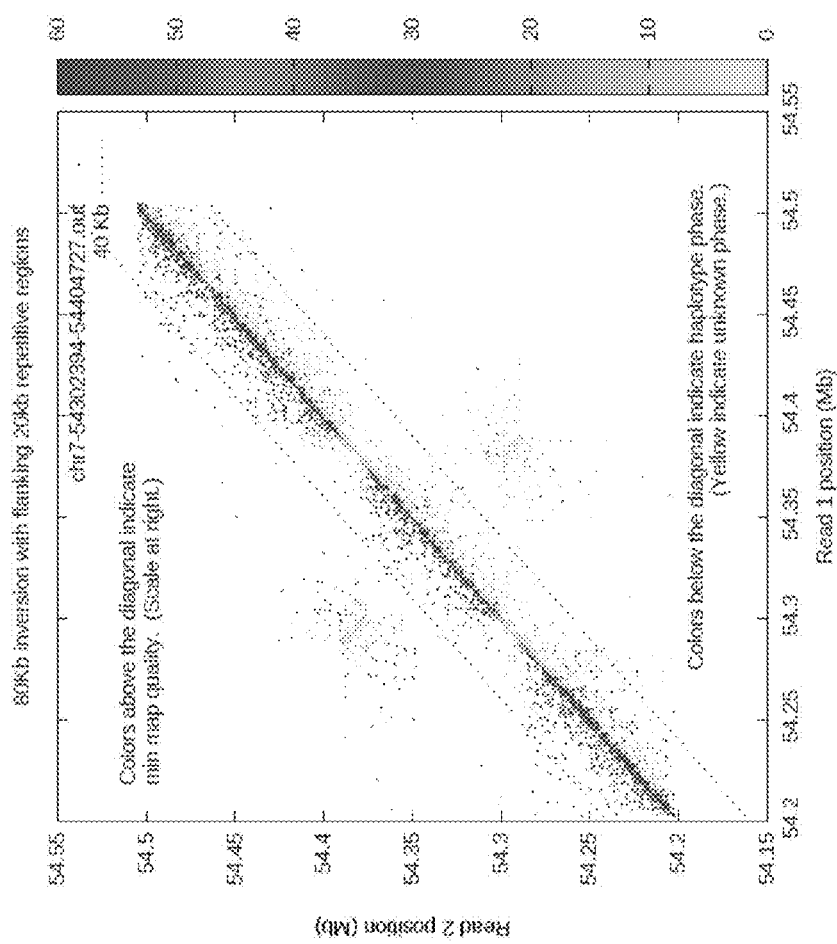
FIGS. 4A and 4B illustrate the mapped locations on the GRCh38 reference sequence of read pairs are plotted in the vicinity of structural differences between GM12878 and the reference.
Figure 4B:
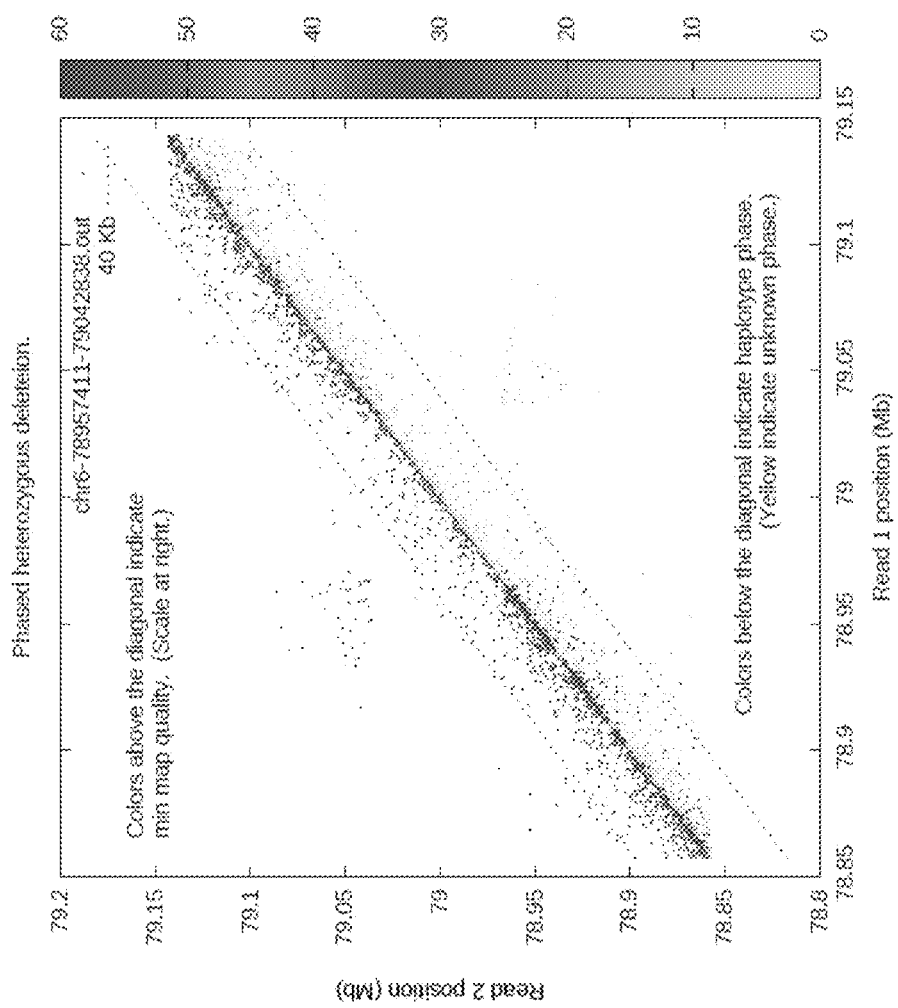

Referring to FIGS. 4A and 4B, an example is provided of mapped locations on a reference sequence, e.g., GRCh38, of read pairs generated from proximity ligation of DNA from re-assembled chromatin are plotted in the vicinity of structural differences between GM12878 and the reference. Each read pair generated is represented both above and below the diagonal. Above the diagonal, shades indicates map quality score on scale shown; below the diagonal shades indicate the inferred haplotype phase of generated read pairs based on overlap with a phased SNPs. In some embodiments, plots generated depict inversions with flanking repetitive regions, as illustrated in FIG. 4B. In some embodiments, plots generated depict data for a phased heterozygous deletion, as illustrated in FIG. 4B.

Figure 5:
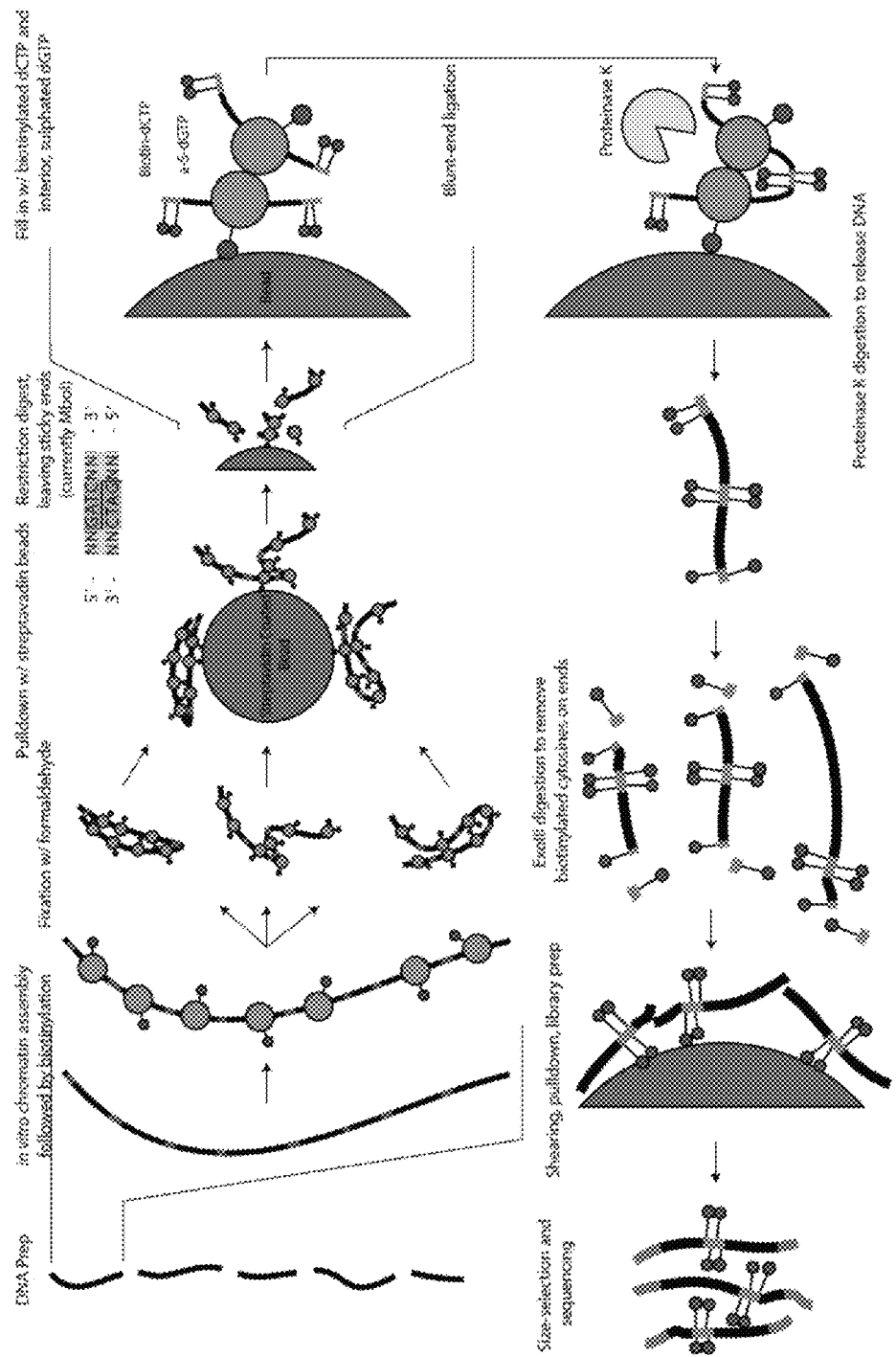
FIG. 5 depicts a flow process for generating material for de novo sequencing.

Referring to FIG. 5, an example is provided of chromatin re-assembly and processing. In some embodiments, purified high molecular weight DNA is subject to in vitro chromatin assembly (with histones and chromatin assembly factors) followed by biotinylation. In some embodiments, the resulting DNA-chromatin complex is then fixated with a fixation agent. In FIG. 5, the fixation agent is formaldehyde. In further embodiments, the DNA-chromatin complex is pulled down with streptavidin beads. In further embodiments, the DNA-chromatin complex is treated with restriction enzyme digestion. As illustrated in FIG. 5, in some cases, the restriction enzyme is MboI. In some cases the restriction enzyme is one that leaves sticky ends, e.g., overhangs in double stranded DNA. In some embodiments, the sticky ends are filled-in with labeled nucleotides. In some cases the labeled nucleotides are biotinylated or sulphated. As illustrated in FIG. 5, in some cases an interior fill-in is performed with sulphated dGTP and an exterior fill-in is done with biotinylated dCTP. In some embodiments, a blunt-end ligation step is performed and the fill-in ends are joined. In some embodiments, the DNA-chromatin complex is subjected to enzymatic digesting to release the DNA from the complex. As illustrated in FIG. 5, in some embodiments the enzyme is proteinase K. In some embodiments, the DNA is treated with a restriction enzyme to remove labeled nucleotides. For example, as illustrated in FIG. 5, treatment with ExoIII digestion removes biotinylated cytosines on ends. In some embodiments, DNA fragments are prepare by for analysis by shearing, pulldown, and use of any Illumina-compatible library generation protocol, but with the removal of normal clean-up steps in-between the reactions, instead substituting a wash and resuspension on the beads.

In various embodiments, the methods and systems of the invention may further comprise software programs on computer systems and use thereof. The computer systems may be programmed to interface between the user.

Figure 6:
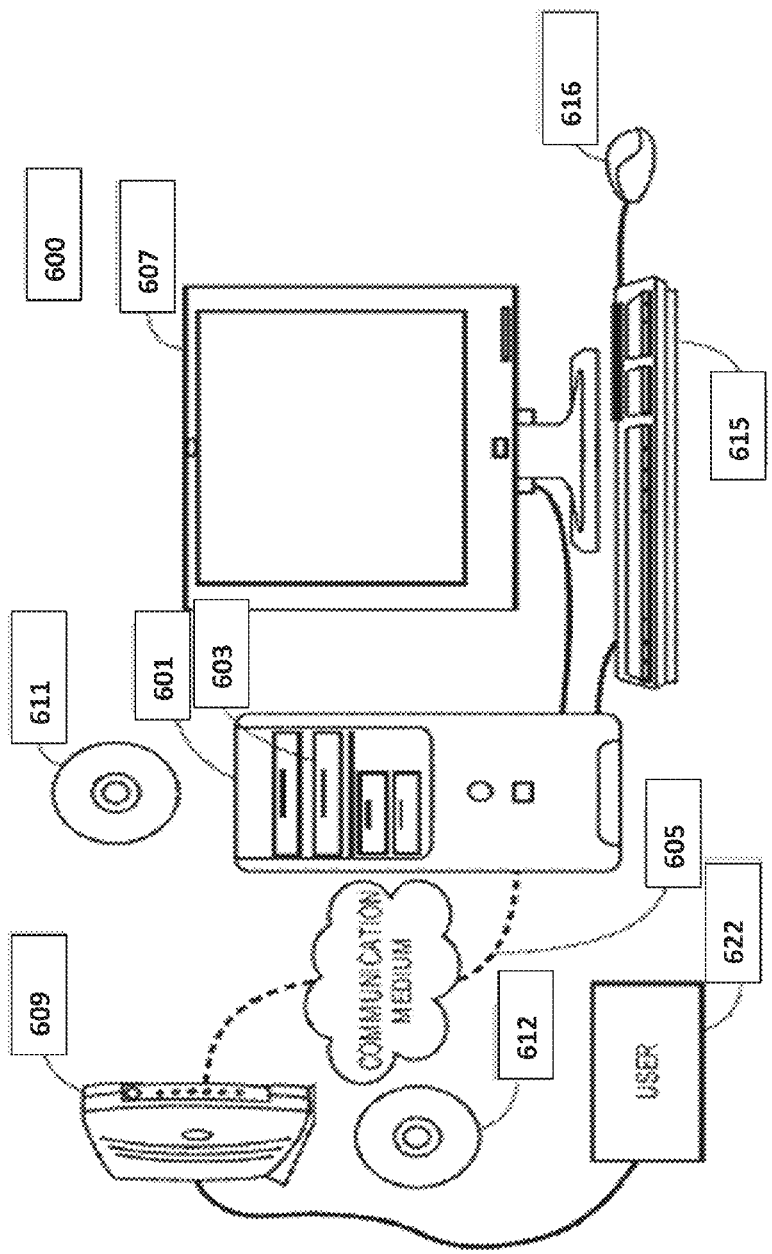
FIG. 6 illustrates an example of a computer system that can be used in connection with example embodiments of the present invention.

The computer system 600 illustrated in FIG. 6 may be understood as a logical apparatus that can read instructions from media 611 and/or a network port 605, which can optionally be connected to server 609 having fixed media 612. The system, such as shown in FIG. 6 can include a CPU 601, disk drives 603, optional input devices such as keyboard 615 and/or mouse 616 and optional monitor 607. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 622 as illustrated in FIG. 6.

Figure 7:
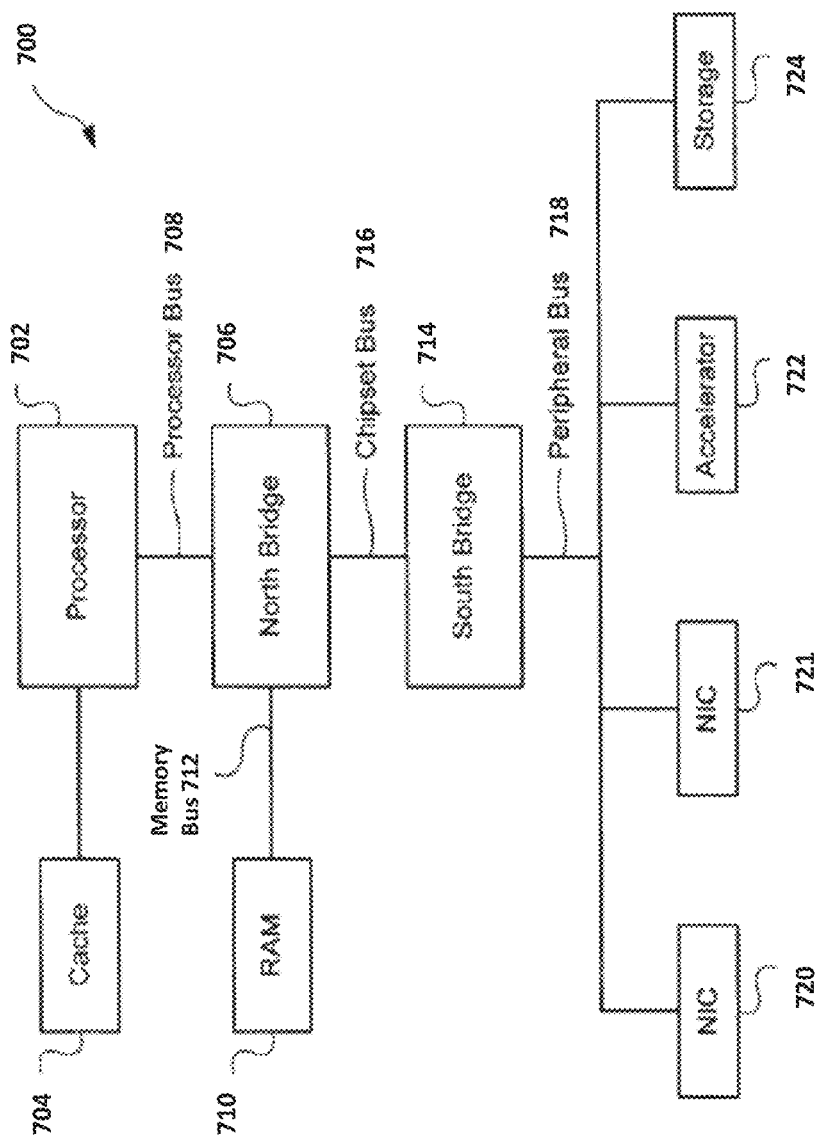
FIG. 7 is a block diagram illustrating a first example architecture of a computer system 2000 that can be used in connection with example embodiments of the present invention.

FIG. 7 is a block diagram illustrating a first example architecture of a computer system 700 that can be used in connection with example embodiments described herein. As depicted in FIG. 7, the example computer system includes a processor 702 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores are used, whether in a single computer system, in a cluster, or distributed across systems over a network comprising a plurality of computers, cell phones, and/or personal data assistant devices.

As illustrated in FIG. 7, a high speed cache 704 can be connected to, or incorporated in, the processor 702 to provide a high speed memory for instructions or data that have been recently, or are frequently, used by processor 702. The processor 702 is connected to a north bridge 706 by a processor bus 708. The north bridge 706 is connected to random access memory (RAM) 710 by a memory bus 712 and manages access to the RAM 710 by the processor 702. The north bridge 706 is also connected to a south bridge 714 by a chipset bus 716. The south bridge 714 is, in turn, connected to a peripheral bus 718. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 718. In some alternative architectures, the functionality of the north bridge can be incorporated into the processor instead of using a separate north bridge chip.

In some embodiments, system 700 includes an accelerator card 722 attached to the peripheral bus 718. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 724 and can be loaded into RAM 710 and/or cache 704 for use by the processor. The system 2000 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example embodiments of the present invention.

In this example, system 700 also includes network interface cards (NICs) 720 and 721 connected to the peripheral bus for providing network interfaces to external storage, such as Network Attached Storage (NAS) and other computer systems that can be used for distributed parallel processing.

Figure 8:
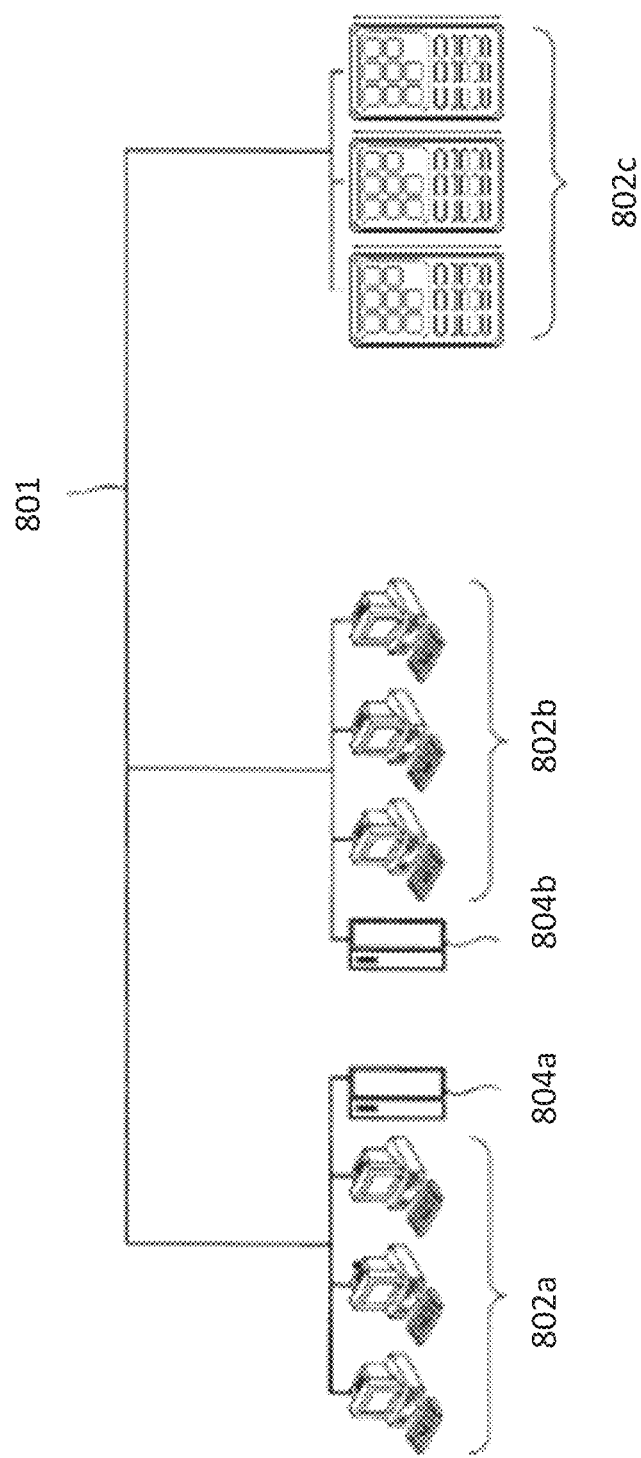
FIG. 8 is a diagram demonstrating a network 800 configured to incorporate a plurality of computer systems, a plurality of cell phones and personal data assistants, and Network Attached Storage (NAS) that can be used in connection with example embodiments of the present invention.

FIG. 8 is a diagram showing a network 800 with a plurality of computer systems 802a, and 802b, a plurality of cell phones and personal data assistants 802c, and Network Attached Storage (NAS) 804a, and 804b. In example embodiments, systems 802a, 802b, and 802c can manage data storage and optimize data access for data stored in Network Attached Storage (NAS) 804a and 804b. A mathematical model can be used for the data and be evaluated using distributed parallel processing across computer systems 802a, and 802b, and cell phone and personal data assistant systems 802c. Computer systems 802a, and 802b, and cell phone and personal data assistant systems 802c can also provide parallel processing for adaptive data restructuring of the data stored in Network Attached Storage (NAS) 804a and 804b. FIG. 8 illustrates an example only, and a wide variety of other computer architectures and systems can be used in conjunction with the various embodiments of the present invention. For example, a blade server can be used to provide parallel processing. Processor blades can be connected through a back plane to provide parallel processing. Storage can also be connected to the back plane or as Network Attached Storage (NAS) through a separate network interface.

In some example embodiments, processors can maintain separate memory spaces and transmit data through network interfaces, back plane or other connectors for parallel processing by other processors. In other embodiments, some or all of the processors can use a shared virtual address memory space.

Figure 9:
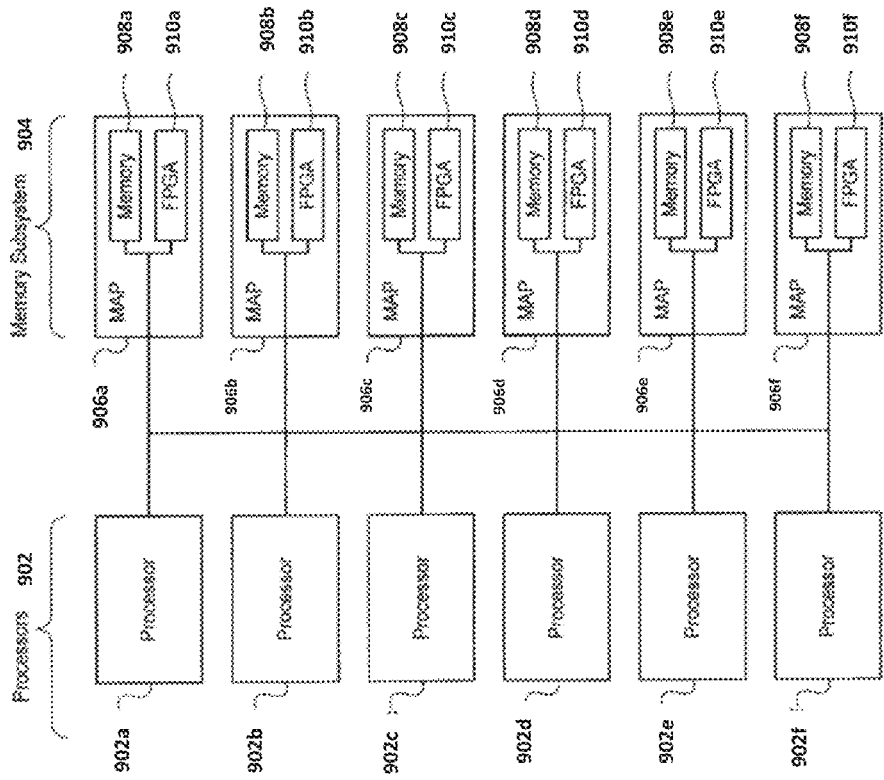
FIG. 9 is a block diagram of a multiprocessor computer system 900 using a shared virtual address memory space that can be used in connection with example embodiments of the present invention.

FIG. 9 is a block diagram of a multiprocessor computer system 900 using a shared virtual address memory space in accordance with an example embodiment. The system includes a plurality of processors 902a-f that can access a shared memory subsystem 904. The system incorporates a plurality of programmable hardware memory algorithm processors (MAPs) 906a-f in the memory subsystem 904. Each MAP 906a-f can comprise a memory 908a-f and one or more field programmable gate arrays (FPGAs) 910a-f. The MAP provides a configurable functional unit and particular algorithms or portions of algorithms can be provided to the FPGAs 910a-f for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 908a-f, allowing it to execute tasks independently of, and asynchronously from, the respective microprocessor 902a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. In some embodiments, all or part of the computer system can be implemented in software or hardware. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer system can be implemented using software modules executing on any of the above or other computer architectures and systems. In other embodiments, the functions of the system can be implemented partially or completely in firmware, programmable logic devices such as field programmable gate arrays (FPGAs) as referenced in FIG. 9, system on chips (SOCs), application specific integrated circuits (ASICs), or other processing and logic elements.

Relative to methods in use at the time of filing the present application, the methods and systems disclosed herein provide a number of advantages.

Some methods and computational systems disclosed herein cluster contigs in a manner independent of the number of chromosomes for the organism. A more conservative threshold on contig-contig links for single-link clustering is applied to assemble the resulting smaller contig clusters into scaffolds, with subsequent scaffolding joining possible by various methods disclosed herein.

In some embodiments, the methods disclosed herein does not essentially involve clustering but goes straight to the spanning tree step, followed by topological tree pruning. In some embodiments, more than one clustering methods can be used, e.g. Markov Cluster Algorithm (MCL algorithm). Without being limited by theory, misassemblies can be prevented by topological pruning by treating these edges with extra care and avoiding assembly misjoins.

After fixing the order of contigs in a scaffold, the orientations can be optimized by using a dynamic programming algorithm. Such approach only read pairs mapping to pairs of contigs adjacent in the ordering contribute to the score being optimized, leaving out any contigs shorter than the maximum separation of good fragment pairs out and unassembled. To improve the orientation step, in addition to nearest-neighbor contig score interactions, contigs that are not nearest-neighbor contig score interactions can be considered by using an algorithm that incorporates data from all pairs mapping to pairs of contigs within at most w-2 intervening contigs, for example, using values of two or greater contigs in the ordering, such as 2, 3, 4, 5, 6, 7, 8, 9, 10 or more than ten.

In some embodiments, the accuracy of intercalation step can be improved. Without being bound by any theory, in assemblies with contigs shorter than the maximum separation between good read pairs after the creation of the trunk, data from contigs within a neighborhood of w contigs along the ordering are included when excluding contigs from the trunk and reinserting into it at sites that maximize the amount of linkage between adjacent contigs.

In some other embodiments, the orientation step can be improved by considering more than nearest-neighbor contig score interactions. After fixing the order of contigs in a scaffold, contig orientations are optimized by using a dynamic programming algorithm. Only read pairs mapping to pairs of contigs adjacent in the ordering contribute to the score being optimized. In some cases, an algorithm that incorporates data from all pairs mapping to pairs of contigs within at most w-2 intervening contigs in the ordering can be used for assemblies with any contigs shorter than the maximum separation of good fragment pairs. For example, using values of two or greater contigs in the ordering, such as 2, 3, 4, 5, 6, 7, 8, 9, 10 or more than ten.

In some embodiments, one can improve both ordering and orientation accuracy by integrating the ordering and orientation steps even more tightly. An initial graph can be constructed such that in this graph, nodes are contig ends, and the two end-nodes of each contig are joined by an edge. The log-likelihood ratio scores of the inter-contig edges under an assumption of a specific short gap size, was computed and followed by sorting. Working down the list in decreasing order of edge score, new edges are either accepted or rejected according to whether they would increase or decrease the total score of the assembly. It is noted that even edges with a positive score could decrease the sum of scores of contigs in the assembly because accepting an edge which implies intercalation of a contig or contigs into the gap of an existing scaffold will increase the gap sizes between pairs of linked contigs on either side of the gap, which will potentially give them a lower score.

In addition, one can efficiently compute maximum likelihood gap sizes. Overall accuracy of the reported assembly can be increased by estimating the length of unknown sequences between consecutive contigs. Given a model of the library creation process that includes a model probability density function (PDF) for the separation d between library read pairs, the maximum likelihood gap length can be found by maximizing the joint likelihoods of the separations $d_i$ of the pairs spanning the gap. For differentiable model PDF, the efficient iterative optimization methods (e.g. Newton-Raphson) can be used.

An element of the methods and compositions disclosed herein is that contigs are assembled into configurations that are local optima among, for example, contig windows of 2, 3, 4, 5, 6, or more than 6 contigs for contig order, orientation or order and orientation, while being executable or obtainable in a relatively short amount of time, such as 8, 7, 6, 5, 4, 3, 2, or less than 2 hours. Thus, in some cases the methods herein allow a high degree of computational power to be brought to a computationally intensive problem without the use of a large amount of computing time and without the need to explore a globally very large computational space. Rather, local ordering achieves a modestly accurate ordering of contigs, and then computational intensity is spent optimizing local windows of contigs rather than globally optimizing all contigs at once in most cases. In some cases, using window sizes that range from 3, 4, 5, or 6, configuration optimization is done in 8, 7, 6, 5, 4, 3, 2, or less than 2 hours. For larger window sizes, configuration optimization is accomplished in a few days up to a week.

Digital Processing Device

In some embodiments, the contig assembly methods described herein include a digital processing device, or use of the same. In further embodiments, the digital processing device includes one or more hardware central processing units (CPU) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). Optionally, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

Some digital processing devices include a display to send visual information to a user, such as a cathode ray tube (CRT), a liquid crystal display (LCD), a thin film transistor liquid crystal display (TFT-LCD), an organic light emitting diode (OLED) display such as a passive-matrix OLED (PMOLED) or active-matrix OLED (AMOLED) display. Plasma displays, video projectors, or combinations of devices such as those disclosed herein.

Often, the digital processing device includes an input device to receive information from a user, such as a keyboard, a pointing device including, by way of non-limiting examples, a mouse, trackball, track pad, joystick, game controller, or stylus. In some embodiments, the input device is a touch screen or a multi-touch screen, a microphone to capture voice or other sound input or a video camera or other sensor to capture motion or visual input. In further embodiments, the input device is a Kinect, Leap Motion, or the like. Often, the input device is a combination of devices such as those disclosed herein.

Non-transitory Computer Readable Storage Medium

In some embodiments, the contig assembly methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the contig assembly methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program implementing the contig assembly methods includes a web application. In light of the disclosure provided herein, those of skill in the art will recognize that a web application, in various embodiments, utilizes one or more software frameworks and one or more database systems. In some embodiments, a web application is created upon a software framework such as Microsoft® NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program implementing the contig assembly methods disclosed herein includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program implementing the contig assembly methods disclosed herein includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Web Browser Plug-in

In some embodiments, the contig assembly methods include a web browser plug-in. In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB .NET, or combinations thereof Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

In some embodiments, the contig assembly methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the contig assembly methods disclosed herein include one or more databases, or use of the same. In view of the disclosure provided herein, those of skill in the art will recognize that many databases are suitable for storage and retrieval of contig information. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

EXAMPLES

Example 1

Genome Finishing Using Paired Reads Generated from Reconstituted Chromatin 5.5 µg of high molecular weight DNA was extracted from the human cell line GM12878 and from the blood of a wild-caught American alligator. The high molecular weight DNA was extracted in fragments of about 150 Kbp. Chromatin was reconstituted by combining the DNA with purified histones and chromatin assembly factors. The reconstituted chromatin was then fixed with formaldehyde and sequence data libraries were generated. FIG. 1 illustrates a schematic of these steps.

For the human GM12878 sample, two DNA libraries were generated using the restriction enzymes MboI and MluCI, which generate 4 bp 5' overhangs. These barcoded libraries were pooled and sequenced on a single Illumina HiSeq 2500 lane in paired 100 bp reads, and generated 46M MboI and 52M MluCI library read pairs. For comparison, a third library was prepared for nominally 40 Kbp DNA, as illustrated in FIG. 2.

For the American alligator genome (*Alligator mississippiensis*), we constructed a single MboI library, sequenced it on a single lane, which resulted in 132M read pairs. To determine the utility of these data for scaffold assembly and haplotype phasing, we aligned the GM12878 library data to the reference human assembly (hg19) (FIG. 2). The libraries generated provided useful linking information up to separations of 150 Kbp on the genome with a background noise rate of approximately one spurious link between unrelated 500 Kbp genomic windows (mean of 0.97 such links). The single lane of sequence from the GM12878 libraries provided linking information equivalent to 3.8×, 8.4×, 8.6×, 18.6×, 13.5×, 6.5× physical coverage in 0-1, 1-5, 5-10, 10-25, 25-50, and 50-200 Kbp libraries respectively, while for alligator the comparable coverage estimates were 5.4×, 16.7×, 16.7×, 42.2×, 36.1×, and 16.5× respectively, as illustrated in FIG. 3.

Example 2

Nucleic Acid Scaffolding Based on Read Pair Data

To determine the power and utility of data extracted from the libraries, contig assembly and scaffolding were conducted using only generic 300-500 bp insert Illumina shotgun libraries and the libraries described above. An 84×, 101 bp paired-end Illumina shotgun data set from GM12878 (Chapman et al., 2011) using MERACULOUS [pmid21876754] into scaffolds with typical (N50) size of 33 Kbp was initially assembled. Read pairs from the generated library were mapped to this initial assembly as described herein. 68.9% of read pairs mapped such that both forward and reverse reads had map-quality >=20 and were thus considered uniquely mapping within the assembly and were not duplicates. 26.8% of these read pairs had forward and reverse reads that mapped to different contigs and were thus potentially informative for further scaffolding of the assembly. The same library data was also used to scaffold a Discovar assembly of 50× coverage in paired 250 bp reads (Sharpe et al., 2015).

A likelihood model was developed to describe how generated libraries sample genomic DNA, and a software pipeline called "HiRise" for breaking and re-scaffolding contigs based on read pair links to contigs. Modeling included a comparison for completeness, contiguity and correctness at local and global scales of the resulting assembly to assemblies of rich WGS datasets, including extensive coverage in fosmid end pairs created by two of the leading WGS assemblers: MERACULOUS (Chapman et al., 2011) and ALLPATHS-LG (APLG) (Gnerre et al., 2011) (Table 1). To avoid the arbitrary choices involved in constructing alignment-based comparisons of assembly quality, comparison was based on the assembled positions of 25.4 million 101 bp sequences that are a randomly selected subset of all distinct 101 bp sequences that occur exactly once in each haplotype of the diploid NA12878 assembly (Rozowsky et al., 2011).

TABLE 1

Table 1: Scaffolding results. Fraction of each assembly in scaffolds containing a misjoin at three different thresholds for identifying misjoins. Scaffold N50. 50 Kbp separation discrepancy 95% confidence interval (95% CI = x means: Given a pair of unique 101-mer tags in the assembly, 95% of them are within 50 Kbp ± x of each other in the reference.) completeness (% C); fraction of 101-mers misoriented.

|  | Misjoins | | | N50 | 95% CI |  | % |
| --- | --- | --- | --- | --- | --- | --- | --- |
|  | 5 Kbp | 10 Kbp | 50 Kbp | (Mbp) | 50 Kbp Δ | % C | misoriented |
| MERACULOUS | 0.032 | 0.030 | 0.022 | 9.1 | 1.3 Kbp | 94.8 | 0.09 |
| APLG | 0.245 | 0.187 | 0.130 | 12.1 | 6.4 Kbp | 92.2 | 0.4 |
| MERAC (33 Kbp N50) + HiRise: | 0.028 | 0.011 | 0.009 | 12.6 | 7.7 Kbp | 94.1 | 1.3 |
| Discovar (178 Kbp N50) + HiRise: | 0.102 | 0.097 | 0.076 | 29.9 | 3.2 Kbp | 97.9 | 1.4 |

Example 3

Determining Long Range Scaffolding Accuracy

The scaffolds that the HiRise pipeline produced were longer and had a lower rate of global mis-assemblies than the published MERACULOUS and APLG assemblies, both of which rely on deep coverage in paired fosmid end reads. Table 1 shows the fraction of the total assembly found in scaffolds containing a misjoin, where a misjoin is defined as having a stretch of unique 101-mers spanning at least 5 Kbp, 10 Kbp or 50 Kbp from more than one chromosome in the diploid reference. The table also shows measures of completeness and contiguity for four successive rounds of HiRise assembly compared to other assemblies of NA12878.

Because the DNA ligation events that create read pairs created by the methods provided herein are not constrained to produce read pairs of defined relative strandedness, contig relative orientations during scaffolding must be inferred from read density information. As a result, the scaffolds arrived at using HiRise calculations had a higher rate of mis-oriented 101-mers (1.3%) than is found in the other assemblies, most occurring in small contigs. The median size of contigs containing mis-oriented 101-mers was 2.1 Kbp.

Example 4

Improved Alligator Assembly

A single DNA fragment library constructed using de novo chromatin remodeling methods described herein for the American alligator (*Alligator mississippiensis*) was generated and sequenced 210.7 million reads on the Illumina HiSeq 2500. Read pairs were mapped to a de novo assembly (N50 81 Kbp) created using publicly available data (Green et al., 2014) and applied the HiRise scaffolding pipeline. The resulting assembly had a scaffold N50 of 10.3 Mbp. To assess the accuracy of these scaffolds, a collection of 1,485 previously generated (Shedlock et al., 2007) bacterial artificial chromosome (BAC) end sequences were aligned to the assembly. Of those 1,298 pairs were uniquely aligned by GMAP (Wu and Watanabe, 2005) with 90% coverage and 95% identity to the contig assembly and the HiRise scaffolded version. In the input assembly, 12.5% of BAC end pairs were captured in the same scaffold with the expected orientation and separation. In the HiRise assembly 96.5% of BAC end pairs were aligned in the same scaffold with 98.1% of BAC end pairs on same scaffold in correct relative orientation. 5 (0.39%) BAC end pairs were placed on the same scaffold but at a distance significantly larger than insert size and 14 (1.08%) were placed on separate scaffolds but far enough from edge of scaffold that distance would be larger than insert size, suggesting a global density of misjoins of less than 1 per 8.36 Mbp of assembly.

Example 5

Assessment of Phase Accuracy

Read pairs where both the forward and reverse read cover a heterozygous site were used to directly read haplotype phase. Because the distance covered in the read pairs generated by de novo chromatin remodeling and fragmenting methods described herein can be as great as the size of the input DNA, the accuracy of phase information and its utility for determining haplotype phase in the GM12878 sample was assessed. Because GM12878 derives from an individual that has been trio-sequenced, reliable haplotype phase information was used to assess the accuracy of phasing information. Read pairs that were haplotype informative and that span between 10 Kbp and 150 Kbp were 99.83% in agreement with the known haplotype phase for GM12878.

Example 6

Identification of Structural Variants

Mapping paired sequence reads from one individual against a reference is the most commonly used sequence-based method for identifying differences in contiguous nucleic acid or genome structure like inversions, deletions and duplications (Tuzun et al., 2005). FIGS. 4A and 4B show how read pairs generated by proximity ligation of DNA from re-assembled chromatin from GM12878 mapped to the human reference genome GRCh38 reveal two such structural differences. To estimate the sensitivity and specificity of the read pair data for identifying structural differences, a maximum likelihood discriminator on simulated data sets constructed to simulate the effect of heterozygous inversions was tested. The test data was constructed by randomly selecting intervals of a defined length L from the mapping of the NA12878 reads generated to the GRCh38 reference sequence and assigning each generated read pair independently at random to the inverted or reference haplotype, and editing the mapped coordinates accordingly. Non-allelic homologous recombination is responsible for much of the structural variation observed in human genomes, resulting in many variation breakpoints that occur in long blocks of repeated sequence (Kidd et al., 2008). The effect of varying lengths of repetitive sequence surrounding the inversion breakpoints was simulated by removing all reads mapped to within a distance W of them. In the absence of repetitive sequences at the inversion breakpoints, for 1 Kbp, 2 Kbp and 5 Kbp inversions respectively, the sensitivities (specificities) were 0.76 (0.88), 0.89 (0.89) and 0.97 (0.94) respectively. When 1 Kbp regions of repetitive (unmappable) sequence at the inversion breakpoints was used in a simulation, the sensitivity (specificity) for 5 Kbp inversions was 0.81 (0.76).

Example 7

DNA Preparation

DNA was extracted with Qiagen Blood and Cell Midi kits according to the manufacturer's instructions. Briefly, cells were lysed, and centrifuged to isolate the nuclei. The nuclei were further digested with a combination of Proteinase K and RNAse A. The DNA was bound to a Qiagen genomic column, washed, eluted and precipitated in isopropanol and pelleted by centrifugation. After drying, the pellet was resuspended in 200 µL TE (Qiagen).

Example 8

Chromatin Assembly

Chromatin was assembled overnight at 27° C. from genomic DNA using the Active Motif in vitro Chromatin Assembly kit. Following incubation, 10% of the sample was used for MNase digestion to confirm successful chromatin assembly.

Example 9

Biotinylation and Restriction Digestion

Chromatin was biotinylated with iodoacetyl-PEG-2-biotin (IPB). Following biotinylation, the chromatin was fixed in 1% formaldehyde at room temperature (RT) for 15 minutes, followed by a quench with 2-fold molar excess of 2.5M Glycine. Excess IPB and cross-linked glycine were removed by dialyzing chromatin in a Slide-A-Lyzer 20 KDa MWCO dialysis cassette (Pierce) against 1 L of dialysis buffer (10 mm Tris-Cl, pH8.0, 1 mM EDTA) at 4° C. for a minimum of 3 hours. Subsequently, the chromatin was digested with either MboI or MluCI in 1× CutSmart for 4 hours at 37° C. The chromatin was again dialyzed in a 50 KDa MWCO dialysis Flex tube (MI Scientific # IB48262) at 4° C. for 2 hours, then again with fresh buffer overnight, to remove enzyme as well as short, free DNA fragments.

Dynabead MyOne C1 streptavidin beads were prepared by washing and resuspending in PBS+0.1% Tween-20, before adding to chromatin and incubating for 1 hour at RT. The beads were then concentrated on a magnetic concentrator rack, before being washed, re-concentrated, and resuspended in 100 µL 1× NEBuffer 2.

Example 10 dNTP Fill-in

To prevent the labeled dNTP's (FIG. 1) from being captured during the fill-in reaction, un-bound streptavidin sites were occupied by incubating beads in the presence of free biotin for 15 minutes at RT. Subsequently, the beads were washed twice before being resuspended in 100 µL 1× NEBuffer 2. Sticky ends were filled in by incubating with dNTPs, including a-S-dGTP and biotinylated dCTP along with 25 U of Klenow (#M0210M, NEB) in 165 µL total volume at 25° C. for 40 minutes. The fill-in reaction was stopped by adding 7 µL of 0.5M EDTA. The beads were then washed twice in Pre-ligation wash buffer (PLWB: 50 mM Tris 7.4; 0.4% Triton X-100; 0.1 mM EDTA), before being resuspended in 100 µL PLWB.

Example 11

Ligation

Ligation was performed in at least 1 mL of T4 ligation buffer at 16° C. for a minimum of 4 hours. A large ligation volume was used to minimize cross-ligation between different chromatin aggregates. The ligation reaction was stopped by adding 40 µL of 0.5M EDTA. The beads were concentrated and resuspended in 100 µL extraction buffer (50 mM Tris-cl pH 8.0, 1 mM EDTA, 0.2% SDS). After adding 400 ug Proteinase K (#P8102S, NEB) the beads were incubated overnight at 55° C., followed by a 2 hour digestion with an additional 200 ug Proteinase K at 55° C. DNA was recovered with either SPRI beads at a 2:1 ratio, a column purification kit, or with a phenol:chloroform extraction. DNA was eluted into Low TE (10 mM Tris-Cl pH 8.0, 0.5 mM EDTA).

Example 12

Exonuclease Digestion

DNA was next digested for 40 minutes at 37° C. with 100 U Exonuclease III (#M0206S, NEB) to remove biotinylated free ends, followed by SPRI cleanup and elution into 101 µL low TE.

Example 13

Shearing and Library Prep

DNA was sheared using a Diagenode Bioruptor set to 'Low' for 60 cycles of 30 seconds on/30 seconds off. After shearing, the DNA was filled in with Klenow polymerase and T4 PNK (#EK0032, Thermo Scientific) at 20° C. for 30 minutes. Following the fill-in reaction, DNA was pulled down on C1 beads that had been prepared by washing twice with Tween wash buffer, before being resuspended in 200 µL 2× NTB (2M NaCl, 10 mM Tris pH 8.0, 0.1 mM EDTA pH 8.0, 0.2% Triton X-100). Once the sample was added, the beads were incubated at room temperature for 20 minutes with rocking. Subsequently, unbiotinylated DNA fragments were removed by washing the beads three times before resuspending in Low TE. Sequencing libraries were generated using established protocols (Meyer and Kircher, 2010).

Example 14

Read Mapping

Sequence reads were truncated whenever a junction was present (GATCGATC for MboI, AATTAATT for MluCI). Reads were then aligned using SMALT [which can be accessed at the website indicated by sanger.ac.uk/resources/software/smalt/] with the -x option to independently align forward and reverse reads. PCR duplicates were marked using Picard-tools MarkDuplicates [which can be accessed at the website indicated by broadinstitute.github.io/picard/]. Non-duplicate read pairs were used in analysis if both reads mapped and had a mapping quality greater than 10.

Example 15

De Novo Assemblies

The human and alligator de novo shotgun assemblies were generated with Meraculous 2.0.3 (Chapman et al., 2011) using publicly available short-insert and mate-pair reads (Simpson and Durbin, 2012; Green et al., 2014). The alligator mate-pair reads were adapter-trimmed with Trimmomatic (Bolger et al., 2014). Some overlapping alligator short-insert reads had been "merged." These were unmerged back into forward and reverse reads.

We claim:
1. A method for nucleic acid sequence data assembly, comprising:
   (a) obtaining purified DNA;
   (b) binding the purified DNA with a DNA binding agent to form DNA/chromatin complexes;
   (c) incubating the DNA-chromatin complexes with restriction enzymes to leave sticky ends;
   (d) performing ligation to join ends of DNA;
   (e) sequencing ligated DNA junctions to generate paired end reads;
   (f) obtaining standard paired-end read distance frequency data;
   (g) obtaining grouped contig sequences; and
   (h) scaffolding the grouped contig sequences such that read pair distance frequency data for read pairs that map to separate contigs approximates the standard paired-end read distance frequency data,
   thereby assembling the sequence data of the nucleic acid.

2. The method of claim 1, wherein read pair distance frequency data for read pairs that map to separate contigs more closely approximates the standard paired-end read distance frequency data when read pair distance likelihood is improved by at least 5% compared to read pair distance likelihood calculated for unscaffolded contig sequences.

3. A method for scaffolding contigs of nucleic acid sequence information obtained from a biological sample, said method comprising:
   (a) obtaining a set of contig sequences having an initial configuration, wherein the contig sequences are obtained by extracting DNA from a biological material and sequencing the DNA;

(b) obtaining a set of paired end reads, wherein the set of paired-end reads is obtained by digesting sample DNA to generate internal double strand breaks within the nucleic acid, allowing the double strand breaks to re-ligate randomly to form a plurality of re-ligation junctions, and sequencing across the plurality of re-ligation junctions;

(c) obtaining standard paired-end read distance frequency data;

(d) grouping contig pairs sharing sequence that coexists in at least one paired end read, thereby generating grouped contigs; and (e) scaffolding the grouped contigs such that read pair distance frequency data for read pairs that map to separate contigs more closely approximates the standard paired-end read distance frequency data by at least 5% relative to the read pair frequency data of the grouped contigs in the initial configuration.

4. The method of claim 3, wherein the sample DNA is crosslinked to at least one DNA binding agent.

5. The method of claim 3, wherein the sample DNA comprises isolated naked DNA.

6. The method of claim 5, wherein the isolated naked DNA is reassembled into reconstituted chromatin.

7. The method of claim 6, wherein the reconstituted chromatin is crosslinked.

8. The method of claim 6, wherein the reconstituted chromatin comprises a DNA binding protein.

9. The method of claim 6, wherein the reconstituted chromatin comprises a nanoparticle.

10. The method of claim 3, wherein the set of paired-end reads are obtained by digesting sample DNA to generate internal double strand breaks within the nucleic acid, allowing the double strand breaks to re-ligate randomly to form a plurality of re-ligation junctions, and sequencing on each side of the plurality of re-ligation junctions.

11. The method of claim 3, wherein standard paired-end read distance frequency data is obtained from paired-end reads where both reads map to a common contig.

12. The method of claim 3, wherein standard paired-end read distance frequency data is obtained from previously generated curves.

13. The method of claim 3, wherein said scaffolding comprises selecting a first set of putative adjacent contigs of said grouped contigs, determining a minimal distance order of said first set of putative adjacent contigs that reduces an aggregate measure of the read-pair distances for said read pairs, and scaffolding said first set of putative adjacent contigs so as to reduce said aggregate measure of the read-pair distance.

14. The method of claim 13, wherein said determining a minimal distance order comprises determining an expected read-pair distance for all possible contig configurations for at least one read pair that comprises reads mapping to two contigs of said first set of putative adjacent contigs.

15. The method of claim 14, comprising selecting a contig orientation from said all possible contig configurations that most improves the read pair distance likelihood compared to other possible configurations from said all possible contig configurations.

16. The method of claim 3, wherein the biological sample comprises a genome.

17. The method of claim 3, wherein the biological sample is a heterogeneous sample comprising a plurality of genomes.

18. A method for scaffolding contigs of nucleic acid sequence information comprising:

(a) obtaining a set of contig sequences having an initial configuration;

(b) obtaining a set of paired end reads;

(c) obtaining standard paired-end read distance frequency data;

(d) grouping contig pairs sharing sequence that coexists in at least one paired end read, thereby generating grouped contigs; and (e) scaffolding the grouped contigs such that read pair distance frequency data for read pairs that map to separate contigs more closely approximates the standard paired-end read distance frequency data by at least 5% relative to the read pair distance frequency data of the grouped contigs in the initial configuration.

19. The method of claim 18, wherein the scaffolding comprises at least one of ordering the grouped contigs, orienting the grouped contigs, merging at least two contigs end to end, inserting one contig into a second contig, and cleaving a contig into at least two constituent contigs.

20. The method of claim 18, wherein read pair distance frequency data for read pairs that map to separate contigs more closely approximates the paired-end read distance frequency data when read pair distance likelihood increases by at least 5% relative to the read pair distance frequency data of the group contigs in the initial configuration.

21. The method of claim 20, wherein read-pair distance likelihood is maximized.

22. The method of claim 18, wherein read pair distance frequency data for read pairs that map to separate contigs more closely approximates the standard paired-end read distance frequency data when a statistical measure of difference between the read pair distance frequency data for read pairs that map to separate contigs and the standard paired-end read distance frequency data decreases by at least 5% relative to the read pair distance frequency data of the grouped contigs in the initial configuration.

23. The method of claim 22, wherein the statistical measure of distance between the read pair distance frequency data for read pairs that map to separate contigs and the standard paired-end read distance frequency data comprises at least one of ANOVA, a t-test, and a X-squared test.

24. The method of claim 23, wherein read pair distance for read pairs that map to separate contigs more closely matches the paired-end read distance frequency data when deviation of read pair distance distribution among ordered contigs obtained as compared to standard paired-end read distance frequency decreases.

25. The method of claim 24, wherein deviation of read pair distance distribution among ordered contigs obtained as compared to standard paired-end read distance frequency is minimized.

26. A method of assembling contig sequence information into at least one scaffold, comprising (a) obtaining sequence information corresponding to a plurality of contigs, obtaining paired-end read information from a nucleic acid sample represented by the plurality of contigs, and (b) configuring the plurality of contigs such that deviation of a read pair distance parameter from a predicted read pair distance data set is decreased by at least 5% compared to the read pair distance parameter of plurality of contigs in an initial configuration, wherein the configuring occurs in less than 8 hours.

27. The method of claim 26, wherein the predicted read pair distance data set comprises a read pair distance likelihood curve.

28. The method of claim 26, wherein the read pair distance parameter is maximum distance likelihood relative to a read pair distance likelihood curve.

29. The method of claim 26, wherein the read pair distance parameter is variation relative to a read pair distance likelihood curve.

30. The method of claim 26, wherein 70% of the plurality of contigs are ordered and oriented so as to match the relative order and orientation of their sequences in the nucleic acid sample in no more than 8 hours.

31. The method of claim 1, wherein an N50 value is increased by at least 1% relative to unscaffolded sequence data.

32. The method of claim 3, wherein an N50 value is increased by at least 1% relative to the grouped contigs in the initial configuration.

33. The method of claim 18, wherein an N50 value is increased by at least 1% relative to the grouped contigs in the initial configuration.

34. The method of claim 26, wherein an N50 value is increased by at least 1% relative to the plurality of contigs in the initial configuration.

* * * * *